(12) United States Patent
Gotthardt et al.

(10) Patent No.: US 8,548,827 B2
(45) Date of Patent: Oct. 1, 2013

(54) COMPUTER-IMPLEMENTED METHOD FOR MEDICAL DIAGNOSIS SUPPORT

(75) Inventors: Frank Gotthardt, Eltelborn (DE); Dierk Helmann, Heidenrod-Kemel (DE)

(73) Assignee: CompuGroup Medical AG, Koblenz (DE)

( * ) Notice: Subject to any disclaimer, the term of this patent is extended or adjusted under 35 U.S.C. 154(b) by 112 days.

(21) Appl. No.: 13/128,185

(22) PCT Filed: Nov. 17, 2009
(Under 37 CFR 1.47)

(86) PCT No.: PCT/EP2009/065333
§ 371 (c)(1),
(2), (4) Date: Dec. 1, 2011

(87) PCT Pub. No.: WO2010/057891
PCT Pub. Date: May 27, 2010

(65) Prior Publication Data
US 2012/0130743 A1   May 24, 2012

(30) Foreign Application Priority Data
Nov. 19, 2008  (EP) .................................. 08169432

(51) Int. Cl.
*G06Q 50/00* (2012.01)
(52) U.S. Cl.
USPC ......... 705/3; 705/2; 706/47; 706/60; 707/600
(58) Field of Classification Search
USPC ...................... 705/2–4; 706/47, 60; 707/600
See application file for complete search history.

(56) References Cited

U.S. PATENT DOCUMENTS

| | | | |
|---|---|---|---|
| 6,149,585 A | 11/2000 | Gray | |
| 7,197,492 B2 * | 3/2007 | Sullivan | 1/1 |
| 7,379,885 B1 * | 5/2008 | Zakim | 705/2 |
| 2002/0002472 A1 * | 1/2002 | Abraham-Fuchs | 705/3 |
| 2003/0158468 A1 | 8/2003 | Iliff | |
| 2003/0212579 A1 * | 11/2003 | Brown et al. | 705/2 |
| 2006/0135859 A1 | 6/2006 | Iliff | |
| 2008/0177578 A1 | 7/2008 | Zakim | |

FOREIGN PATENT DOCUMENTS

| | | |
|---|---|---|
| WO | 0057264 A1 | 9/2000 |
| WO | 0209580 A1 | 2/2002 |

OTHER PUBLICATIONS

Lai, F., Macmillan, J., Daudelin, D. H., & Kent, D. M. (2006). The potential of training to increase acceptance and use of computerized decision support systems for medical diagnosis. Human Factors, 48(1), 95-108. Retrieved from http://search.proquest.com/docview/216443272?accountid=14753.*
International Preliminary Report on Patentability for corresponding PCT application PCT/EP2009/065333, May 19, 2011.
Shortlife E H, et. al. "Biomedical Informatics: Computer Applications in Health Care and Biomedicine" pp. 46-79, XP002570368 ISBN: 978-0-387-28986-1, May 25, 2006.

(Continued)

*Primary Examiner* — Mark Holcomb
(74) *Attorney, Agent, or Firm* — Matthew B. Dernier, Esq.; Gibson & Dernier LLP

(57) ABSTRACT

The invention relates to a computer-implemented method for medical diagnosis support for patient data of a patient through a data processing system, wherein the data processing system comprises a graphical user interface and a database containing rules for calculating diagnosis risks.

12 Claims, 19 Drawing Sheets

(56) References Cited

OTHER PUBLICATIONS

Janssen B, et. al. "Guidelines based on decision Support Software; Quality management in neurological outpatient schizophrenia treatment" vol. 77, No. 5, pp. 567-575, XP019415519 ISSN: 1433-0407, May 1, 2006 (Translation enclosed).

Anonymous "IBM WebSphere Applet Designer Guide passage" pp. 95-113, XP002268915, Aug. 1, 2000.
International Search Report for corresponding PCT application PCT/EP2009/065333, Apr. 12, 2010.
Musen, M.A. et. a., "Clinical Decision-Support Systems," pp. 698-736, Biomedical Informatics (Jamuary 2006).

* cited by examiner

Patients

References

COPD (J44.99)

Satisfied scan criteria for this fundamental risk
- Match with ICD F17
- Your patient falls into the 70-74 age group Ascertainment of fundamental risk on basis of:
- Shahab L, Jarvis MJ, Britton J, West R. Prevalence, diagnosis and relation to tobacco dependence of chronic obstructive pulmonary disease in a nationally representative population sample. Thorax 2006; 61(12): 1043-7.

Symptom diagnostic on the basis of:
- Lokke A, Lange P, Scharling H, Fabricius P, Vestbo J, Developing COPD: a 25 year follow up study of the general population. Thorax 2006; 61(11): 935-9.
- Global Initiative for Chronic Obstructive Lung Disease (GOLD). Global strategy for the diagnosis, management and prevention of chronic obstructive pulmonary disease. Executive summary.2007.http://www.goldcopd.com/Guidelineitem.asp?l1=28l2=1&intId=1816.[10.01.2008].

Guideline diagnostic on the basis of:
- North Rhine Association of Statutory Health Insurance Physicians. Overview of the criteria of diagnosis verification for the participation of patients in the asthma/COPD DMP. http://www.kvno.de/importiert/einschreibekri_asthma_copd.pdf [24.10.2008].

Back

700 — Rules for calculating first diagnosis risks

| Rule ID | Medication | ICD | LEZ | Age | Sex | Diagnosis ID | Effect on diagnosis risk |
|---|---|---|---|---|---|---|---|
| 1987 | 0 | F32 | 54 | 35-45 | m | 23 | 15.23 |
| 1988 | 0 | | 23 | 15-30 | f | 23 | 12.9 |
| 1989 | 0 | F32 | | 65-85 | m | 23 | 64.12 |
| 1990 | 377 | F44 | | | | 442 | 0.22 |
| 1991 | 0 | K59.9 + F44 | | 65-80 | f | 442 | x 1.67 |

Fig. 6

800 — Symptom diagnostic

| Symptom ID | Description | Diagnosis ID | Effect on diagnosis risk |
|---|---|---|---|
| 1321 | Alcohol level 0.05-0.1% | 68 | 15.23 |
| 1322 | Alcohol level 0.1-0.15% | 68 | 12.9 |
| 1323 | Repeated clashes with the law on account of alcohol consumption | 68 | 64.12 |
| 1324 | Signs of paralysis | 444 | x 1.22 |
| 1325 | Impaired speech | 444 | 0.67 |

Fig. 7

900 — Guideline diagnostic

| Guideline criteria ID | Description/ Guideline routine | Diagnosis ID | Effect on diagnosis risk |
|---|---|---|---|
| 1421 | Alcohol level 0.05-0.1% | 68 | 15.23 |
| 1422 | Alcohol level 0.1-0.15% | 68 | 12.9 |
| 1423 | Repeated clashes with the law on account of alcohol consumption | 68 | 64.12 |
| 1424 | Signs of paralysis | 444 | 0.22 |
| 1425 | Impaired speech | 444 | x 1.22 |
| 1426 | <!Java Script Code_326 --> ... | 443 | |
| 1427 | <!Java Script Code_327 --> ... | 443 | |
| 1428 | <!Java Script Code_328 --> ... | 758 | |
| 1429 | <!Java Script Code_329 --> ... | 68 | |
| 1430 | <!Java Script Code_330 --> ... | 356 | |

Fig. 8

COMPUTER-IMPLEMENTED METHOD FOR MEDICAL DIAGNOSIS SUPPORT

BACKGROUND

The invention relates to a computer-implemented method for medical diagnosis assistance, to a data processing system and to a computer program product.

Medical information systems document diverse, patient-related, administrative and medical data, inter alia. Although the use of medical information systems means that the opportunities which are available to a treating doctor for documenting patient data allow essentially uninterrupted recording and storage of the patient data, time problems which often arise in doctor's practices and hospitals give rise to the problem that a treating doctor is only rarely capable of obtaining a full overview of the course of treatment for a patient by looking through the patient record for the patient before a treatment appointment for said patient begins. In this case, a treating doctor often merely has time to deal intensively with health disorders and diagnoses for the patient which have occurred in the very recent past.

However, a further cause of the limited review capability of the doctor can also be found in the typical design of graphical user interfaces for medical information systems. To illustrate a patient datasheet, such information systems indicate merely the most recently input medical diagnoses and pointers on account of the limited presentation opportunities of a graphical user interface. Although a doctor could obtain access to further diagnoses which are a relatively long period in the past by "scrolling" through the patient history, that is to say by moving a scrollbar, he can do this only rarely in detail, as outlined at the outset, for reasons of time. The doctor is therefore unable to obtain a general overview of the history of illness of a patient in a short time using medical information systems.

As a consequence, the problem arises that much information which is held implicitly in the electronic patient record and would be useful for diagnosis and the prescription of medicaments is not used. Chronic illnesses, which are manifested by recurring symptoms of illness, for example, are not recognized by the treating doctor, since the doctor—on the basis of the presentation of the patient's treatment history on his graphical user interface—does not easily obtain information regarding whether, by way of example, there are constantly recurring illness symptoms and diagnoses in the patient's illness history which could provide a pointer to the presence of a relevant chronic illness. Medicaments which the patient permanently takes, or examinations or operations which have occurred in the past and which could provide an influence as to his previous illnesses, are likewise often overlooked by the doctor during diagnosis. Many patients do not themselves have a broad overview of the medicaments and active ingredients which they regularly take, which means that the patients often cannot provide any reliable information about their history of illness. The relationships between various diagnoses made in the past can be so complex and the knowledge which needs to be processed may be so extensive that not even a relatively long period of dealing with the electronic patient record would prevent important relationships from being overlooked, especially since medical knowledge is continually changing. However, a comprehensive check on the treatment history in terms of the systems and findings for the patient individually for each patient before an appointment of treatment is impossible in practice in terms of time anyway.

Besides the time aspect, there are many other factors which stand in the way of fast and reliable diagnosis by the doctor. A symptom associated with an illness, e.g. headache, can occur with different degrees of manifestation from patient to patient. In this case, a symptom may be an indication of a multiplicity of different illnesses, and each illness may be characterized by a set of several, not always implicit, symptoms. In addition, the available specialist medical knowledge is very unevenly distributed for the various illnesses. The causes and symptoms of some illnesses are known generally and described adequately, whereas the causes of other illnesses are still totally unclear. For some illnesses, at least correlation studies are available which show a statistical relationship for certain environmental factors, dietary habits, physical activity, a particular genotype or the presence of further illnesses (comorbities). Some illnesses can be clearly associated with one or a few causes, e.g. monogenetically hereditary illnesses can be associated with a genetic defect. Other illnesses are multifactorially conditional and can be caused by a multiplicity of factors. By way of example, arthritis of the joints may be conditional upon age-related and abrasion-related wear on the joints. However, arthritis of the joints may also be the consequence of a corresponding genetic predisposition that has an effect starting from a certain age. Furthermore, diagnosis is also complicated by the circumstance that there are various methods of diagnosis possible for establishing an illness. Thus, besides taking account of the current symptoms of a patient within the context of his history of illness, there are also methods of diagnosis and query standards based on a guideline diagnostic specific to the respective illness which are recommended by medical insurance companies.

SUMMARY OF THE INVENTION

The term "diagnosis" subsequently denotes a finding concerning a physiological state or an illness in a patient. A diagnosis has conventionally been made by a doctor using externally recognizable features (symptoms), laboratory values or various diagnostic methods, said doctor has assessed these data against the background of his medical training and experience. A fundamental advantage of the present method according to the invention is that these assessment steps can take place automatically and can take account of more information than a doctor is able to in the shortness of time. By using the method according to the invention, the doctor is thus able to improve the quality of the diagnoses made and to speed up diagnosis.

The invention is based on the object of rendering a user of a medical information system able to analyze patient data for the presence of illnesses more reliably, more efficiently and faster.

A challenge from a technical point of view is presented particularly by the high level of complexity and heterogeneity of the factors which need to be used for calculating risk, and also the compelling requirement for even a multiplicity of complex queries on a large data record for electronic patient records to be able to be performed quickly (use in a clinic). Whereas nothing may be known for an illness apart from a simple correlation, and the risk calculation method may be correspondingly simple, there may be several highly complex risk calculation methods for other illnesses, since they have been examined adequately and many studies are available. A diagnosis system which can be used in practice must be able to accept this heterogeneity of the risk calculation methods and also frequent changes in the methods of calculation. The system must also be able to allow for the practical problems of diagnosis by the doctor (limited available time, unclear symptoms).

The object on which the invention is based is achieved by means of the features of one or more embodiments disclosed and/or described herein.

The invention relates to a computer-implemented method for medical diagnosis assistance for patient data for a patient by a data processing system. The data processing system has a graphical user interface. The method starts by accessing rules for the calculation of diagnosis risks for medical diagnoses. The rules and the data objects representing the diagnoses are stored in a database in a manner which allows for the heterogeneity described above for the knowledge of various illnesses and symptoms which accompany them.

Each diagnosis in this database is stored in connection with a medical primary risk. The medical primary risk for a diagnosis indicates the probability with which the presence of this diagnosis in a patient can be assumed if the only knowledge used for this assumption is the general statistical distribution of an illness in the overall population. The primary risk of the presence of an illness by which 10 000 people in a population group of 1 million people are affected is thus 0.01 (1%). Age, sex or previous illnesses are not taken into account for the calculation of the primary risk. On the contrary, the primary risk based on the currently available medical knowledge (number of illnesses per overall population or, if unknown, number of ill people within an examined group of patients in a medical study) is used. A reference to the literature source from which the value for the primary risk has been taken is likewise stored in the database.

A prediction system according to the invention is not only capable of associating a primary risk with each diagnosis. In accordance with one preferred embodiment of the invention, medical diagnosis risks are calculated individually for a patient on the basis of personal risk factors for a multiplicity of possible diagnoses. This is done by applying rules to the data from the patient. Each rule contains one or more query conditions (relating to age, sex, previous medical history, inter alia). The application of a rule to the data in an electronic patient record means checking whether all the query conditions for a rule are satisfied for this data record. The rules are stored in a database such that a multiplicity of possible query conditions can be taken into account flexibly in different combinations. The database scheme used also allows by loading of appropriate updates for the medical diagnosis objects and risk calculation methods, so that the method according to the invention can easily be matched to the current and constantly changing level of medical knowledge. The application of the rules to the patient data results in the calculation of at least one first medical diagnosis risk for a first medical diagnosis if at least one of the rules can be applied to the patient data. This means that if the database contains three rules for calculating a risk for a particular illness K, all three of which contain a patient age of at least 30 years as one condition, then in this example it is not possible to apply any of the rules to a 25-year-old patient. If it was possible to apply at least one rule, the next step involves the output of the first calculated diagnosis risk for the first medical diagnosis together with the first medical diagnosis on the graphical user interface and the output of a user query regarding whether an interactive symptom diagnostic and/or a guideline diagnostic needs to be performed for the first medical diagnosis. Medical guidelines are systematically developed diagnostic and symptom assessment methods to assist decision-making by doctors. Both the symptom diagnostic and the guideline diagnostic are used firstly to define the first diagnosis risk calculated by applying the rule more precisely by interactively indicating further features of the patient. Secondly, they provide the doctor with proposals for symptoms and guideline criteria for selection which are stored in association with the first diagnosis. These guideline criteria and symptoms in turn may correlate to other diagnoses which are proposed to the doctor likewise for selection. By selecting and deselecting the symptoms and guideline criteria linked to a first diagnosis risk, it is thus not only possible to define the first diagnosis risk more precisely, it is also possible to detect further possible diagnoses within the context of the first diagnosis which the doctor can select for further analysis.

In the event of an interactive symptom diagnostic needing to be performed for a first medical diagnosis, a symptom user query is output which allows the doctor to stipulate which of the medical symptoms linked to the first medical diagnosis are used for a further analysis of the patient data and are intended to influence the previously determined diagnosis risk. As a result of the presented symptoms being selected and deselected by the user, the first diagnosis risk calculated in the preceding step is modified and is defined more precisely. Depending on which symptoms are actually present in the examined patient in the opinion of the doctor, the doctor selects some or else all of the proposed symptoms. Each selection or deselection of a symptom can increase or reduce the first diagnosis risk. The symptom user query can thus be used by the doctor to define the first diagnosis result, which is based on the application of rules, more precisely. The second diagnosis risk determined in the symptom diagnostic thus uses the first diagnosis risk as a starting value in order to define said first diagnosis risk more precisely according to the presence or absence of further symptoms. Finally, a subsequent step involves the output of the second, even more precise, diagnosis risk together with the second diagnosis on the graphical user interface.

If, in addition or as an alternative to the symptom diagnostic, a guideline diagnostic is intended to be performed then a guideline diagnostic user query is output. If the guideline diagnostic occurs immediately after the calculation of the first diagnosis risk, the first diagnosis risk is the starting value for the further more precise definition of the diagnosis risk. If the guideline diagnostic is executed after the symptom diagnostic, the second diagnosis risk ascertained in the symptom diagnostic is the starting value for the further more precise definition of the diagnosis risk. The diagnosis risk calculate in the course of the guideline diagnostic is called the third diagnosis risk, regardless of the order in which the diagnosis steps are actually performed. Similarly, the diagnosis risk ascertained in the symptom diagnostic is called the second diagnosis risk. The symptom diagnostic is thus not a prerequisite for the performance of the guideline diagnostic. On the contrary, both methods of diagnosis can take place on the basis of one another or individually directly after calculation of the first diagnosis risk.

Symptoms which the doctor can use on the basis of a guideline diagnostic in order to assess the presence of a particular diagnostic are subsequently called guideline criteria. The guideline criteria are stored in a first database in combination with the diagnosis objects. The performance of a guideline diagnostic for a diagnosis means that the user is presented with the guideline criteria associated with this diagnosis for a selection. The guideline criteria may also comprise laboratory values for the patient, e.g. the blood sugar value, the serum creatine value, the blood pressure or similar data. The user, normally that is to say the doctor, selects from the presented set of guideline criteria some which are considered relevant and which are intended to be used for further more precise definition of the previously determined diagnosis risk. As a result of selection and deselection of the presented guideline criteria by the user, the diagnosis risk calculated in the preceding step is modified and defined more precisely to an even greater degree. Depending on what guideline criteria are actually present in the examined patient in the view of the doctor, the doctor selects some or else all of the proposed guideline criteria. The selection or deselection of individual guideline criteria results in modification of the starting risk value, as a result of which a third diagnosis risk is returned and displayed. In addition to the selection and deselection of guideline criteria by the doctor, the third diagnosis risk is defined even more precisely by virtue of the application of illness-specific guideline routines. Guidelines routines are calculation routines which are specific to a diagnosis and which ultimately result in modification of the second diagnosis risk value. By way of example, the guideline routines may weight the presence of individual guideline criteria more heavily, perform complex Boolean operations (e.g. AND, OR, NOR) or arithmetic functions on the selected guideline criteria and apply the resulting modified diagnosis risk. Often, the guideline routines on the guideline criteria for diagnosis risk calculation are heuristics based on combinations of several individual factors. The MDRD formula frequently used for the diagnosis of kidney function disorders, for example, takes account not only of the creatine value in the serum (laboratory finding) but also of the age, skin color and sex of the patient. That is to say factors for which it is known from various studies that they can influence the presence of kidney function disorders or can at least correlate thereto. ICD codes (international statistical classification of illnesses and related health problems) and performance coefficients LEZ (e.g. based on the standard scale of assessment for medical fees, EBM) for previous illnesses and diagnoses can also be considered as further factors in a rule. ICD codes represent diagnoses which have already been made in the patient's past on the basis of the patient record. Since the occurrence of some illnesses in the past has a positive correlation to an increased risk of the occurrence of other illnesses, it may be useful to consider this factor in the rules when calculating risk. LEZ codes can also assist the calculation of the diagnosis risk, even though they are not always appointed to a particular previous illness. If the patient has visited a doctor in the past with uncertain upper abdomen complaints, for example, and the doctor then performed a gastroscopy without any findings, then this event in the patient record is not linked to a diagnosis for an illness. The fact that a gastroscopy was performed in the first place, which can be seen from the LEZ code, may be an indication of the presence of health problems in the upper abdomen area, however. The third diagnosis risk determined in the guideline diagnostic thus uses the second diagnosis risk as a starting value in order to define it more precisely according to the presence or absence of guideline criteria associated with the diagnosis and according to the result of the guideline routines. Finally, a subsequent step involves the third diagnosis risk calculated in this manner being output together with the third medical diagnosis on the graphical user interface.

By confirming the suspected diagnosis, which may be based on the calculation of the first, second or third diagnosis risk, the doctor can, in accordance with one preferred embodiment of the invention, confirm the diagnosis, which is consequently stored in the electronic patient record for the patient.

In accordance with one preferred embodiment of the invention, the calculation of one or more first diagnosis risks by applying the rules is initiated immediately whenever the doctor or a surgery assistant opens the electronic patient record. By contrast, the calculated diagnosis risks can also be displayed later, e.g. only when the doctor opens a prescription form. This embodiment is particularly advantageous because, in everyday practice, the electronic patient record is typically opened by a doctor's assistant first, for example in order to enter laboratory values or administrative data associated with the visit to the doctor. Since the opening of the electronic record initiates the risk calculation, the results are already available to the doctor, which produces a further time saving. The doctor can immediately skip to the symptom diagnostic or guideline diagnostic.

In accordance with a further embodiment, the diagnoses obtained by applying the rules and further patient-related data are presented in a popup window. So as not to overload the doctor with a large number of windows, the use of a threshold value for the calculated diagnosis risk, for example, allows the effect to be achieved that only information which is actually relevant is displayed. Furthermore, a maximum number of popup windows which are intended to be displayed to the user per unit time can be defined in the system according to the invention.

In addition to the automatic diagnosis by the diagnosis method according to the invention, one embodiment of the present invention provides the opportunity for a suspected diagnosis check. This function involves the doctor being able to directly input a diagnosis into the system as a suspected diagnosis. This option ensures that even if the system does not propose a diagnosis, the doctor can make a closer examination of a supposition regarding the presence of a particular diagnosis. The suspected diagnosis check differs from the practice explained above in that rules which are applied to the patient data do not propose the first diagnoses, but rather this is done by the doctor. The doctor selects a suspected diagnosis from a list of possible diagnoses in the first database. In the next step, he can define his suspicion more precisely by applying the symptom diagnostic and/or guideline diagnostic and can possibly reject the suspected diagnosis or accept it into the patient record as verified.

Patient data are subsequently understood to mean any kind of information which has been recorded for a patient. This includes not only structured and free-text data but also electronic image data and medical measurement data of any kind. Structured patient data are understood to mean patient data which have been provided on the basis of a previously stipulated standard or classification. This includes particularly, but unexclusively, the use of ICD codes, of central pharmaceutical numbers (PZNs) and of LEZs according to the standard scale of assessment for medical fees (EBM) and also specific contents of medical provision (KV) forms such as transfers, referrals, work in capacity certificates or the like.

The method according to the invention has the advantage that a treating doctor is rendered able to take account of various medical diagnoses at large at one stretch. In other words, he is thus able to analyze the patient data faster and more efficiently. Furthermore, the method allows a doctor to be automatically pointed to possible medical diagnoses which are not recognizable upon manual examination of the patient data, since this requires complex relationships between medical findings to be taken into consideration. The cited method therefore displays medical diagnosis risks and associated diagnoses ascertained individually for the patient to a doctor. If the doctor is of the view that a possible diagnosis might have a high level of relevance in the present case which he is treating, he is thus able, by confirming the user query regarding whether an interactive symptom diagnostic is intended to be performed for the first medical diagnosis, to quickly and effectively determine, in a guided manner, whether or not a displayed medical diagnosis is actually relevant. In other words, he is therefore able to confirm or reject a suspicion of a determined diagnosis. Overall, this ensures that the time for interaction between the doctor and the data processing system is substantially shortened. The same applies in the similar manner to the guideline diagnostic too.

In accordance with one embodiment of the invention, the user has the opportunity in the symptom user query to select various medical symptoms which are linked to the first medical diagnosis for the purpose of further analysis of the patient data. Following the selection of a symptom which he considers to be relevant to the currently examined patient, the symptom diagnostic rules associated with this selected symptom are applied to the previously determined diagnosis risk value for a determined diagnosis. The symptom user query is of interactive design, that is to say that the doctor can use individual symptoms which he believes to be found on the patient for the diagnosis or can exclude them from the diagnosis. This has the advantage that the doctor can interactively ascertain the influence of every single symptom on the diagnosis result individually by selecting and deselecting the symptom. Often, the presence of a symptom is not explicit (slight headache, slight flushes, which could also be brought about by clothing, unspecific complaints or symptoms which do not fit into the context of other symptoms). In such cases, it is very useful for the doctor to be able to perform a risk calculation for various medical diagnoses both excepting and including individual symptoms, since the doctor is thereby able to establish whether a diagnosis would also have been made without considering a particular, uncertainly diagnosed symptom.

In accordance with one embodiment of the invention, the user has the opportunity to select various guideline criteria, which may also include laboratory values which are linked to the previously determined diagnosis, for a further analysis of the patient data in a similar manner for the guideline diagnostic. Following the selection of the guideline criterion which he considers relevant to the currently examined patient, the previously determined risk value for a particular diagnosis is modified, the level of the modification being dependent on the respective guideline criterion. The guideline user query is of interactive design, that is to say that the doctor can use individual guideline criteria which he believes to have been found on the patient for the diagnosis or can exclude them from the diagnosis. In addition, the previously determined diagnosis risk is modified by the execution of diagnosis-specific guideline routines.

In accordance with one embodiment of the invention, the patient data are received from a second database. In this case, said second database may be a database which is external to the data processing system, such as the database in a doctor information system.

In accordance with one embodiment of the invention, medical diagnoses are output only starting from a predetermined threshold value. Furthermore, the medical diagnoses are output preferably in a manner sorted on the basis of the calculated risk level. This ensures that a user of the data processing system, i.e. a treating doctor, is not unnecessarily confronted by irrelevant medical diagnoses. Typically, a threshold value of 40% is chosen for a diagnosis risk which is to be displayed to the doctor, but this value can be altered by the user.

In accordance with one embodiment of the invention, the first, second and third medical diagnosis risks are displayed in the form of a tachograph disk. Preferably, this involves the diagnosis risk being displayed using color shades on the scale of the tachograph disk. Additionally, in accordance with one embodiment of the invention, the primary risk is displayed as a risk probability in the form of a numerical value together with the tachograph disk. Hence, a user is able to intuitively appreciate the risk of the presence of a particular medical diagnosis so as subsequently to take an appropriate decision about whether or not this diagnosis needs to be pursued in detail in a manner which is efficient in terms of time.

In accordance with a further embodiment of the invention, a first operator control element is displayed together with the first medical diagnosis risk, wherein the first operator control element is designed for user confirmation, wherein in the event of user confirmation the first operator control element is used to store the first medical diagnosis and/or the medical symptoms in combination with the patient data in the second database. This renders a doctor able to include a medical diagnosis which appears to him to be verified, possibly together with the symptoms which he has input, in a patient database as well, so that when the patient record is called again the doctor is again able to access such a medical finding as part of the patient record.

In accordance with a further embodiment of the invention, together with the second medical diagnosis risk, a second operator control element is displayed, wherein the second operator control element is designed for user confirmation, wherein in the event of user confirmation using the second operator control element the second diagnosis risk and the second medical diagnosis are output as a new first diagnosis risk and as a new first medical diagnosis on the graphical user interface. In other words, this provides the opportunity to update the diagnosis which has been defined in more detail by virtue of the additional input of symptoms in that overview which was produced originally with the output of the first diagnosis risk for the first medical diagnosis together with the first medical diagnosis. This is relevant particularly to the situation in which not only a single medical diagnosis was originally displayed with the provision of an appropriate diagnosis risk but also a set of different diagnoses. The performance of the symptom user query firstly defines more precisely the risk of that diagnosis for which the symptom diagnostic was performed. Furthermore, the symptom diagnostic has the function of ascertaining further possible relevant diagnoses which were not included in the list of the first diagnoses. This is done such that the user of the symptom diagnostic is shown further diagnoses which correlate to the symptoms selected by the user. If the user considers the additionally proposed diagnoses to be relevant, he can select the diagnoses and thereby add them to the list of the first diagnoses. By virtue of dynamic adaptation of the first diagnosis risks on the basis of the patient data and all the input symptoms, a highly precise and updated overview of possible risk probabilities of the symptoms is thus displayed clearly.

In accordance with one embodiment of the invention, every user selection of a further medical symptom is followed by the symptom diagnostic rules again being applied to the patient data and the medical symptoms chosen by the user to date. Subsequently, at least one new second diagnosis risk for a new second medical diagnosis is dynamically calculated afresh, followed by updated output of the freshly calculated new second diagnosis risk together with the new second medical diagnosis on the graphical user interface. Finally, there is updated output of the user query regarding which medical symptoms linked to the new second medical diagnosis are intended to be used for further analysis of the patient data. Hence, the doctor is able to immediately recognize what significance the specific indication of an individual symptom has for possible diagnoses in respect of the diagnosis risks thereof.

In accordance with a further embodiment of the invention, the updated output of the second diagnosis risk prompts fresh updated output of the symptom user query, wherein the updated output of the symptom user query indicates which of the medical symptoms linked to the further medical diagnosis previously selected by the user is intended to be used for a further analysis of the patient data, with medical symptoms previously chosen by the user being retained in the updated output of the symptom user query. In other words, this further restricts the list of selectable possible medical symptoms or dynamically adds further possible selectable symptoms to it. By way of example, this is relevant when the combined evaluation of patient data and chosen symptoms provide an indication that there is a possible illness which can be considered for a diagnosis risk calculation only when considering further, previously unindicated symptoms, however.

In accordance with a further embodiment of the invention, the symptom user query is made in the form of a checkbox list.

In accordance with a further embodiment of the invention, the first and/or second database is/are a database which is external to the data processing system, or the first and/or second database is/are contained in the data processing system.

In accordance with a further embodiment of the invention, the computer-implemented method for assisting diagnosis is implemented as a plug-in for an interface, wherein the interface can interchange data with a multiplicity of doctor information systems (AISs). Since the plug-in uses this interface to communicate with the widest variety of AISs, the application thereof is not limited to one specific AIS. On the contrary, the plug-in can be used for a multiplicity of AISs.

In accordance with a further embodiment of the invention, at least some of the laboratory values for a patient are input automatically, e.g. by virtue of the link to an LIMS (labor information and management system). In this case, the data transmission is effected preferably on the basis of the LOINC (logical Observation Identifiers Names and Codes) system for the encryption and transmission of data from laboratory examinations.

In accordance with a further embodiment of the invention, all structured medical data from the electronic patient records of a doctor or of a clinic are statistically evaluated. This involves the patients and the medical data associated therewith being divided into strata (groups whose representatives resemble one another in terms of certain features, e.g. in terms of age, sex, profession/income, physical activity, available diagnoses, etc.). Data mining and inference methods are used to ascertain relationships between these features and the risk of occurrence of further diagnoses from said strata. These methods can be used to reveal statistical relationships which are not known in medicine to date. The correlation data obtained in this manner can be used to define the rules for calculating diagnosis risks even more precisely and better.

In accordance with a further embodiment of the invention, the method also comprises the step of conditioning the patient data, wherein the rules are applied to the patient data only for the conditioned patient data. The data conditioning comprises, inter alia, the filtering of structured data from the patient data. This reduces the volume of data which is to be handled and transmitted for each query and significantly speeds up the relevant query.

In accordance with a further embodiment of the invention, the patient data are read from a second database and conditioned, which particularly involves the filtering of the structured data from all the available patient data. The conditioned patient data are subsequently stored in a third database, the rules being applied to the patient data by accessing the third database. Again, the third database may be a database which is external to the data processing system. However, the third database is preferably a cache memory in the data processing system, so that a query for the relevant patient data can be made very quickly. Particularly when the method according to the invention is used by a server/client system, this is a significant advantage, since for appropriate queries the first and third databases can be kept relatively small in size—the volume of data to be transmitted or the number of queries to be made is therefore drastically reduced. A further technical advantage of loading all structured patient data in the cache memory is that this "memory database" ensures that the patient data are always available in the same structure, even if the structure of the patient data in the second database, for example, is dependent on the AIS or LIMS used and said data may be structured differently.

In accordance with one embodiment of the invention, at least some of the patient data are displayed in a first display window of the graphical user interface, wherein the first and second diagnosis risks for a first and a second medical diagnosis are output together with the medical diagnosis on the graphical user interface in a popup.

In accordance with a further embodiment of the invention, the rules are applied to the patient data automatically after the patient data have been displayed in the first display window.

In accordance with a further embodiment of the invention, the method is performed after the electronic patient record has been opened, with the method also comprising the step of receiving new patient data by virtue of a user input.

In accordance with a further embodiment of the invention, the structured data obtained during the doctor's diagnosis using the method according to the invention can be used to automatically produce doctor's letters. Following the performance of a symptom diagnostic which resulted in the diagnosis of an illness based on the presence of five symptoms, the system can automatically—for example—produce a doctor's letter which contains the information that a particular patient was present in the practice on a particular date, the relevant five symptoms were found in the patient and that, on the basis of these symptoms, a particular diagnosis was made. The automated production of doctor's letters and other administrative documents allows the efficiency of the workflows in a doctor's practice to be increased significantly and allows errors as a result of manual input of the diagnoses into the doctor's letter to be avoided.

In a further aspect, the invention relates to a data processing system having a graphical user interface, wherein the data processing system is designed to perform the method for medical diagnosis assistance for a patient.

In a further aspect, the invention relates to a computer program product having instructions—which can be executed by a processor—for performing the method for medical diagnosis assistance for patient data for a patient.

In accordance with a further embodiment of the invention, the graphical user interface has at least a first and a second display window. In this context, the method comprises the step of displaying at least some patient data for a patient in the first display window, wherein the displayed patient data are displayed in the first display window row by row. The first display window is designed for row-by-row tracking of the patient data that are to be displayed by a scrollbar. First of all, a first database is accessed, said first database containing the medical diagnosis objects. The medical diagnosis objects are linked to rules for the patient data from the patient and are used for automatically ascertaining individualized diagnosis risks on the basis of the electronic patient record. The first database also contains information about whether the illnesses represented by the medical diagnosis objects are chronically pronounced as a rule or in individual cases. First of all, the check is performed to determine whether at least one of the rules is satisfied for the patient data. If this is the case then a display element is displayed on the graphical user interface, the display element having at least one of the first diagnosis objects for which the first rule is satisfied. If the first diagnosis determined in this manner is recorded in the first database as a possible permanent diagnosis (chronic illness), a user query is output on the graphical user interface regarding whether a medical diagnosis link to the diagnosis object needs to be accepted as a chronic permanent diagnosis. If the medical diagnosis linked to the diagnosis object does need to be accepted as a permanent diagnosis, the permanent diagnosis is displayed in the second display window regardless of the position of the scrollbar. This ensures that the doctor can scroll freely to the patient record without losing the important information from the permanent diagnoses from his field of vision, since the second display window does not have its position altered by the scrolling movement, of course. This has the advantage that a treated doctor can be assisted in quickly and efficiently making diagnoses for chronic illnesses in a patient. The treating doctor no longer needs to look through all of the patient data which are available to him for a patient in complex fashion, especially since this is usually not possible for reasons of time, as already noted above.

It should be noted that the method also comprises the storage of the permanent diagnosis in the second database, which also contains the patient data, in combination with the patient data. As a result, a treating doctor is able, even when just the last entry in the patient record is displayed in the first display window, to be immediately informed about the presence of such a crucial diagnosis of a chronic illness when the patient record is called afresh too.

It should also be pointed out that "diagnosis object" is understood to mean any kind of information which allows a medical diagnosis to be described. This includes free-text information, which addresses the diagnosis by name, for example, or which provides the detailed description of a clinical picture that accompanies the chronic illness. In addition, diagnosis objects also include the ICD codes already mentioned above or generally structured information, however.

In accordance with one embodiment of the invention, the graphical user interface also has a third display window, wherein the method—if the medical diagnosis linked to the diagnosis object is intended to be accepted as a permanent diagnosis—also comprises the following steps: first of all, it is found that in this embodiment the first database contains information about what active ingredients need to be prescribed when a diagnosis is available. In addition, the first or a fourth database contains information about what medicaments and associated medicament objects contain what active ingredients. In addition, the electronic patient record contains information about what medicaments have been prescribed for the patient in the past.

First of all, when the doctor has confirmed that the present illness/diagnosis is a chronic diagnosis, the first database is searched for active ingredients which can be prescribed when this diagnosis is available. In addition, said active ingredients are associated with the medicaments (or medicament objects representing them), and the electronic patient record is analyzed to determine whether medicaments have prescribed in the past which contain this active ingredient. If this is the case, a further display element is displayed on the graphical user interface, said further display element having at least one of the medicament objects which have already been prescribed previously and which can also be used for treating a permanent diagnosis in the patient. Next, a further user query is output on the graphical user interface regarding whether a medicament linked to the medicament object is intended to be accepted as a preparation for a permanent medication. If the medicament linked to the medicament object is intended to be accepted as a preparation for permanent medication then, after appropriate user confirmation, the permanent medication is permanently displayed so as to be visible in the third display window, likewise regardless of the position of the scrollbar.

In other words, if the medical diagnosis linked to the diagnosis object is intended to be accepted as a permanent diagnosis, that is to say if a chronic illness is assessed by the doctor as verified, then the further step of checking whether medicaments already used to treat the chronic illness have previously been prescribed to the patient on the basis of the patient record, that is to say the patient data, is performed. If the system detects a relevant chronic illness and if there are active ingredients or medicaments in the individual patient record which fit in with these chronic illnesses, it is proposed to the doctor that he accept the respective preparation in the "permanent medication" category in the third display window. As a further condition before a diagnosis is proposed to the doctor as a permanent diagnosis, it is also possible to check whether the calculated diagnosis risk exceeds a threshold value. This query may also be absent from other embodiments of the invention, however. In this case too, a complex and time-consuming search for appropriate medicaments or active ingredients in the patient data is again dispensed with, which in turn renders the doctor capable of quickly and efficiently analyzing the patient data which are stored in an appropriate database. This method also ensures that the doctor is provided with an indication of the presence of a chronic illness and possibly of permanent medication if he has incorrectly made a one-off diagnosis, even though the patient record would actually have revealed that a chronic illness is involved.

In accordance with a further embodiment of the invention, the permanent medicaments confirmed by the doctor can be stored in combination with the patient data as permanent medication.

In accordance with a further embodiment of the invention, the first and/or second and/or fourth database is/are a database which is external to the data processing system, but it is also possible for the first and/or second and/or fourth database to be contained in the data processing system itself. In accordance with a preferred embodiment, however, the patient data are located in the second database, for example a doctor information system. The first database is identical to the second and fourth databases and is provided together with the aforementioned data processing system, for example.

In a further alternative variant, it is also possible for the second database to be contained in a doctor information system, said doctor information system being able to perform the method according to the invention as described above. In order to perform the method, the doctor information system uses a network to access a web service which can be retrieved from a server. This web service provides a service, for example in the form of a servlet, which allows the method according to the invention to be applied to the patient data. In general, although it is possible for the web service to access the first and fourth databases, which are external databases in respect of the doctor information system, the web service can either be performed on the doctor information system or can be performed at the server end on a server which is operated by a medical service provider. In this case, the first and fourth databases may be associated with said server of the medical service provider. Regardless of the use of web services, the method according to the invention can also be performed on an external server, the graphical user interface being part of a client which is used to input patient data and which can be controlled by an appropriate doctor.

In accordance with a further embodiment of the invention, the rules for determining the first diagnosis risk are linked to a time constant for a maximum age of the patient data. The time constant comprises at least the date and possibly further time details which denote when a data entry was made in the electronic patient record, the data entry being able to render the making of a particular diagnosis, the prescription of a medicament or the performance of or billing for a medical examination. In accordance with this embodiment of the invention, the check to determine whether the patient record contains pointers to the presence of a diagnosis, particularly a permanent diagnosis, is applied only to the patient data which have a more recent time stamp than the maximum age. By considering the time stamp, the doctor can determine that only such diagnoses, medicaments and treatments in the patient record as have been entered into the record within a predetermined period are significant for the diagnosis. In addition, this can prevent diagnoses of the same kind which have arisen several times in the past at long intervals of time from being incorrectly interpreted as the presence of a chronic illness. This predetermined period is initially prescribed by the system, but it can also be adjusted as appropriate by the doctor. Furthermore, this predefined period is preferably dependent on the type of medical diagnosis, so that the time constant is stipulated individually for each query condition. Nevertheless, it is possible to stipulate a global maximum limit for the age of the patient data under consideration.

In accordance with a further embodiment of the invention, the check to determine whether some of the rules for calculating first diagnosis risks can be applied to the patient data is performed automatically after the at least one portion of the patient data has been displayed in the first display window. Furthermore, the method is preferably performed in real time, said method also comprising the step of receiving new patient data by virtue of appropriate user input. In summary, this affords the advantage that a treating doctor is reliably informed—in principle immediately and directly either after the patient record is opened or after appropriate patient data have been input into the patient record—of whether his patient is at risk of having a chronic illness.

In accordance with a further embodiment of the invention, the check to determine whether at least one of the first rules is satisfied for the patient data is performed in the order of decreasing diagnosis risk for the respective rule. Hence, not all rules which are available need to be applied to the patient data, but rather the query for the rules can be made on the basis of the aforementioned prioritization. By way of example, such prioritization may also involve only those rules which are linked to the highest diagnosis risk being respectively implemented for a particular diagnosis.

If a rule implemented on the basis of this prioritization pertains, the query for further rules for the same diagnosis can remain unmade, since a relatively high risk value is no longer to be expected for this diagnosis, even when further rules pertain. This can further shorten the computation time required for risk calculation.

In a further aspect, the invention relates to the function of the medicament prescription aid. In accordance with this embodiment, the medicament objects in the first database are stored with information about pack size (number of dosage units present in the pack, measured in milliliters, drops, tablets or other units, for example). In addition, each medicament object is provided with a piece of information about the standard dosage, that is to say information about how many dosage units per day, week or month normally need to be taken. In accordance with this supplementary function, when the patient record is opened, the medicament objects prescribed to the patient in the past are read and also the information about pack size and about the dose prescribed as standard which is stored in combination with these medicament objects. Using the date of the last prescription, which can be read from the patient data, the medicament prescription aid function can calculate how long the prescribed medicament is still sufficient and whether the doctor may need to prescribe a further pack.

In accordance with one preferred embodiment, this medicament prescription aid relates primarily to permanently prescribed medicaments. The indication of the time which still remains until the prescription of a further pack is necessary is preferably displayed in the form of a color-coded scale or tachograph disk, with red signaling that the medicament now needs to be represcribed, green signaling that the currently prescribed pack is still sufficient, and yellow signaling that the repeat prescription is a matter left to the discretion of the doctor.

In a further aspect, the invention relates to a data processing system having a graphical user interface, wherein the data processing system is designed to perform the method for displaying patient-related diagnoses of chronic illnesses.

In a further aspect, the invention relates to a computer program product having instructions which can be executed by a processor for the purpose of performing the method according to the invention for displaying patient-related diagnoses of chronic illnesses.

BRIEF DESCRIPTION OF THE DRAWINGS

Embodiments of the invention are explained in more detail below with reference to the drawings, in which.

DETAILED DESCRIPTION OF THE INVENTION

In the text which follows, elements which are similar to one another are identified by the same reference symbols.

Figure 1:
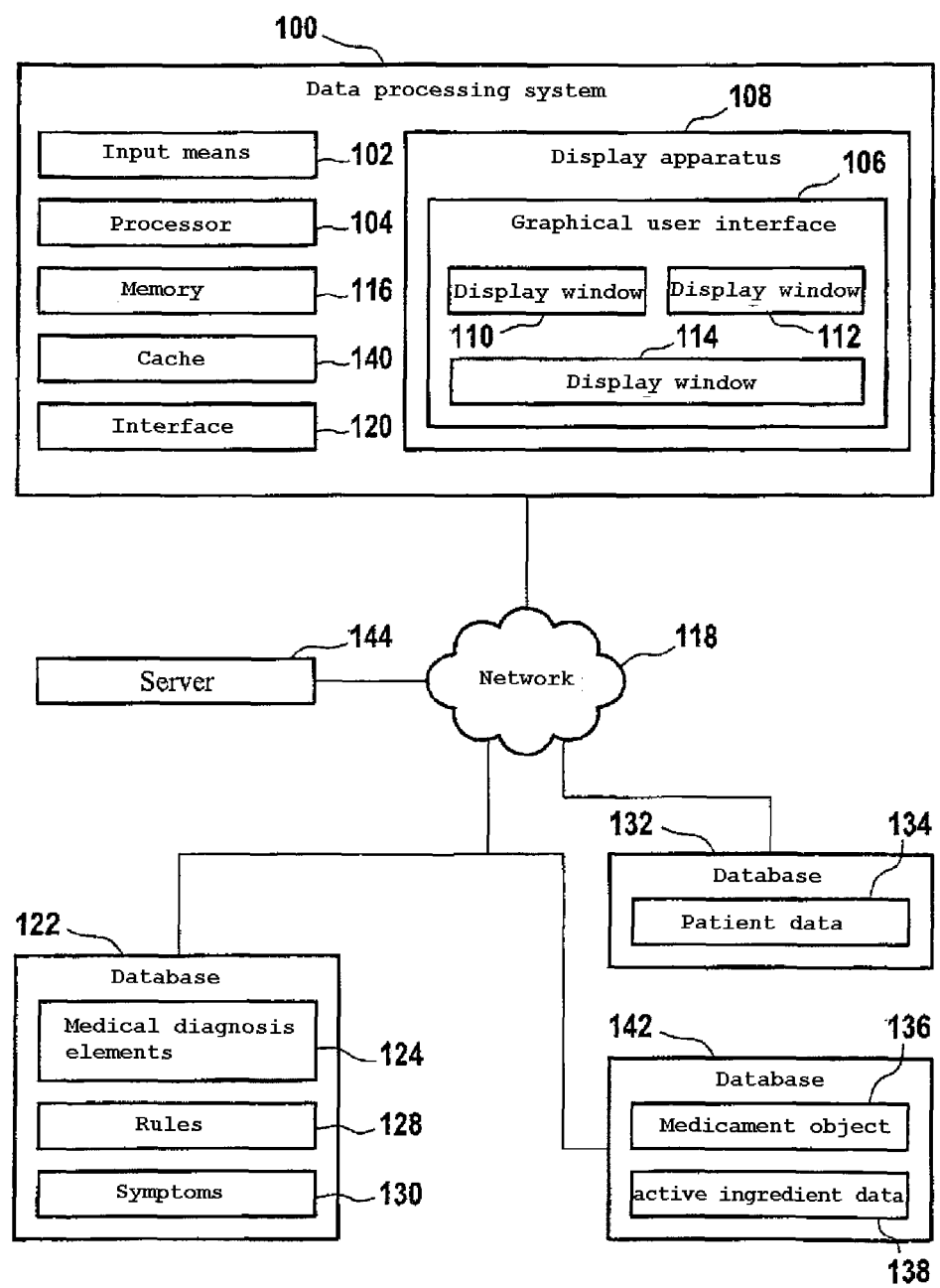
FIG. 1 shows a block diagram of a data processing system according to the invention.

FIG. 1 shows a block diagram of a data processing system 100 according to the invention. The data processing system 100 has a processor 104 and input means 102, such as a mouse, keyboard, etc. The input means used may also be medical engineering appliances which can be used to capture and store appropriate medical image and/or measurement data for a patient. In addition, the data processing system 100 has a memory 116 which contains a computer-executable code for an application program, for example for performing the method according to the invention. Furthermore, the data processing system 100 has a graphical user interface 106 which is output on an appropriate display apparatus 108. By way of example, said display apparatus 108 may be an LCD or CRT screen.

Using an interface 120, the data processing system 100 can communicate with databases 122, 132 and 142, for example via the network 118. In one preferred embodiment of the invention, the interface communicates with the doctor information system AIS using a data encryption method, e.g. a hash method. However, the databases 122, 132 and 142 may also be part of the data processing system 100 itself. Furthermore, the code for executing by the processor 104 can also be retrieved from a server 144, in which case the code for performing the method according to the invention is provided by means of a web service, for example. The code can be executed either on the server 144 or else in the data processing system 100.

It will subsequently be assumed that the databases 122, 132 and 142 are external databases and that also the method is performed directly on the data processing system 100 by the processor 104. To this end, a treating doctor first of all opens a patient record. Said patient record contains patient data 134 which is stored in the database 132. For this purpose, the patient data 134 are now first of all transmitted via the network 118 to the data processing system 100. The most recently input patient data are then presented row by row in the display window 114, said display window having a scrollbar. This means that by moving the scrollbar the doctor is able to scroll through all entries in the patient data.

However, since a treating doctor is typically unable—for reasons of time—to reliably obtain an overview of the entire illness history of a patient, the procedure by the data processing system 100 or the processor 104 thereof after the patient record has been opened is now first of all such that the network 118 is used to access the database 122. This database 122 contains medical diagnosis objects 124.

By checking whether at least one of the rules 128 is satisfied for the patient data 134, the data processing system 100 is able to ascertain whether there is possibly a high level of probability of the presence of a chronic illness in the patient. The first database 122 contains information about which of the medical diagnosis objects occur or may occur as permanent diagnoses. If one of the rules 128, which ascertains the diagnosis risk for the presence of a particular diagnosis on the basis of the patient data 134, is satisfied and if the diagnosis object ascertained in this manner is stored in the first database as a possible permanent diagnosis, then a display element, for example a popup, is displayed on the graphical user interface 106. This popup contains further information regarding the possibility of the presence of a chronic illness, and hence particularly information which is contained in the medical diagnosis object 124. By way of example, this may be an ICD code or the name of a corresponding chronic illness. Furthermore, additional further information and possibly also links in the form of hyperlinks to further databases can be specified which the treating doctor can use to obtain further detailed information about the relevant chronic illness.

When a corresponding display element in the form of a popup, for example, or else in the form of any other display element has been displayed on the graphical user interface, the data processing system 100 provides the treating doctor with the opportunity to put the relevant chronic illness into the "permanent diagnosis" category, that is to say to have said diagnosis displayed permanently in the display window 110 of the graphical user interface 106, specifically regardless of scroll movement within the various rows of the patient data in the display window 114. If such action is confirmed by the doctor, this permanent display of the medical diagnosis, for example in the form of an ICD code, in the display window 110 then preferably occurs and furthermore said display option is stored for the patient in his patient record in the database 132. In other words, the patient data 134 are thus complemented by the permanent diagnosis "chronic illness". When the patient record is next opened by the treating doctor, the data processing system 100 is thus able to present said permanent diagnosis directly in the display window 110 on a permanent basis.

When the medical diagnosis linked to the diagnosis object has been accepted as a permanent diagnosis, the data processing system 100 first of all accesses the database 122, which contains information regarding what active ingredients normally need to be prescribed when a particular diagnosis has been made. In a subsequent step, the database 142 is accessed. The database 142 comprises medical medicament objects 136 and information about what active ingredients 138 are contained in what medicaments. The access to the database is used to ascertain those medicament objects which, on the basis of the association information for active ingredient and medicament, contain the active ingredients which need to be prescribed when a particular diagnosis has been made, according to the information from the database 122. In the next step, the patient data 134 are analyzed to determine whether one or more of the medicaments associated in this manner have already been prescribed for the patient in the past. If it has been possible to find relevant entries in the patient data, that is to say that the patient has already been treated with one of these medicaments, an appropriate user query is output on the graphical user interface 106. Said graphical user interface is in turn used to present the ascertained medical medicament objects, for example in the form of active ingredients or preparation names, possibly by virtue of PZN numbers, whereupon the treating doctor can select one or more medicaments which he wishes to add to the patient record for the purpose of permanent medication for the respective patient from the list which is thus available to him. Following the selection of one or more medicaments, these are then presented permanently in the display window 112 of the graphical user interface 106.

In accordance with a further embodiment of the invention, the list of preparations proposed by the doctor as permanent medication is not limited to those preparations which have already been prescribed, which means that for the described function can also be used to ascertain suitable medicaments for treating a chronic illness which have not yet been prescribed to date.

The data processing system 100 allows a treating doctor to continue to make diagnoses reliably, however. By way of example, to this end the data processing system 100 can again access the database 122 in order to retrieve rules 128 therefrom to calculate diagnosis risks for medical diagnoses, the database 122 also storing the medical diagnoses in combination with medical symptoms 130. By applying the rules 128 to the patient data 134 and calculating a diagnosis risk for a first medical diagnosis, said diagnosis risk can be displayed to the doctor on the graphical user interface 106, again in the form of a popup, for example. In this case, the diagnosis risk is presented to the doctor preferably together with the medical diagnosis. In general, various risks of various medical diagnoses, thus made, can be displayed at this juncture, preferably sorted on the basis of risk probability. So as not to unnecessarily confuse the doctor with improbable diagnosis risks, diagnosis risks are preferably displayed only starting from a certain threshold value, which is freely scalable. This has the further advantage that it is possible to operate with system resource savings, since in this case not all irrelevant diagnoses need to be kept permanently in the memory of the data processing system.

Following the output of the one diagnosis risk or possibly of the plurality of diagnosis risks for medical diagnoses, a user query is output on the graphical user interface 106 regarding whether an interactive symptom diagnostic needs to be performed 610 for this medical diagnosis and whether a guideline diagnostic needs to be performed 646 additionally or instead of the symptom diagnostic. If the latter is confirmed by the doctor, a symptom user query is output regarding which of the medical symptoms 130 linked to the medical diagnosis need to be used for further analysis of the patient data 134. By way of example, a diagnosis chosen by the doctor has various illness symptoms displayed in the form of a list containing checkboxes, the diagnosis risk being dynamically updated and recalculated for the relevant diagnosis finding whenever a checkbox is activated, that is to say that the presence of an illness symptom is confirmed. If necessary, the diagnosis finding can also be complemented by further still more precise diagnosis findings on the graphical user interface. By way of example, if a medical diagnosis initially read merely "60% risk of diabetes", it is now possible—as a result of the additional more precise definition—for the graphical user interface 106 to output that the risk of "diabetes type I is 80%" and the "risk of diabetes type II is 40%".

If a treating doctor now considers one of the medical diagnoses to be verified, he can confirm this accordingly and therefore store it in the database 132 in combination with the patient data 134.

Figure 2:
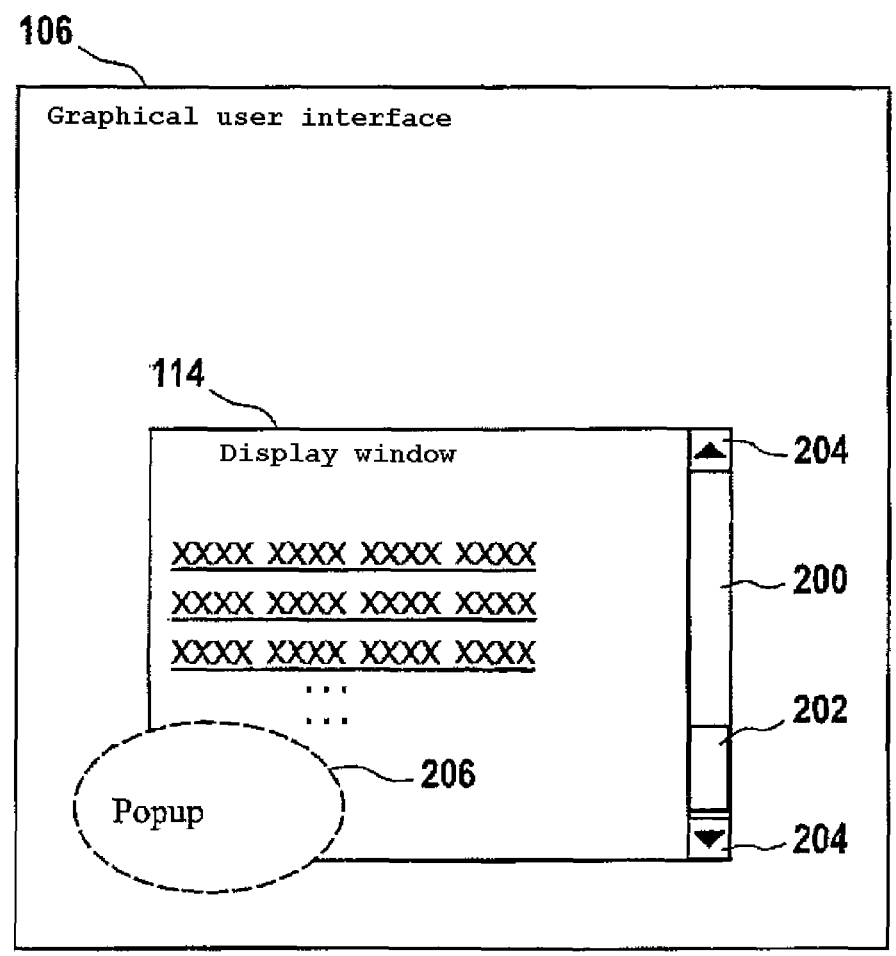
FIG. 2 shows a schematic view of a graphical user interface.

FIG. 2 shows a schematic view of a graphical user interface 106. As already discussed for FIG. 1, the graphical user interface 106 has display windows 110, 112 and 114. The display window 110 is used to display permanent diagnoses, whereas the display window 112 is designed to display permanent medications.

The display window 114 is used for displaying patient data row by row, with only the few, most recently made entries into a patient record being displayed, preferably when the patient record is opened. Nevertheless, access to further entries is possible by virtue of an appropriate element 202 of a scrollbar 200 being moved vertically up and down, so that it is possible to scroll through the various entries in the patient record. By clicking on arrows 204, it is also possible to perform scrolling in the form of row hops. In addition, FIG. 2 shows a popup 206 in which a user can be provided with further information. By way of example, such a popup may be a display element with diagnosis objects, queries, medicament objects or else diagnosis risks in connection with medical diagnoses, a window for performing an interactive symptom diagnostic or an appropriate query window.

Figure 3:
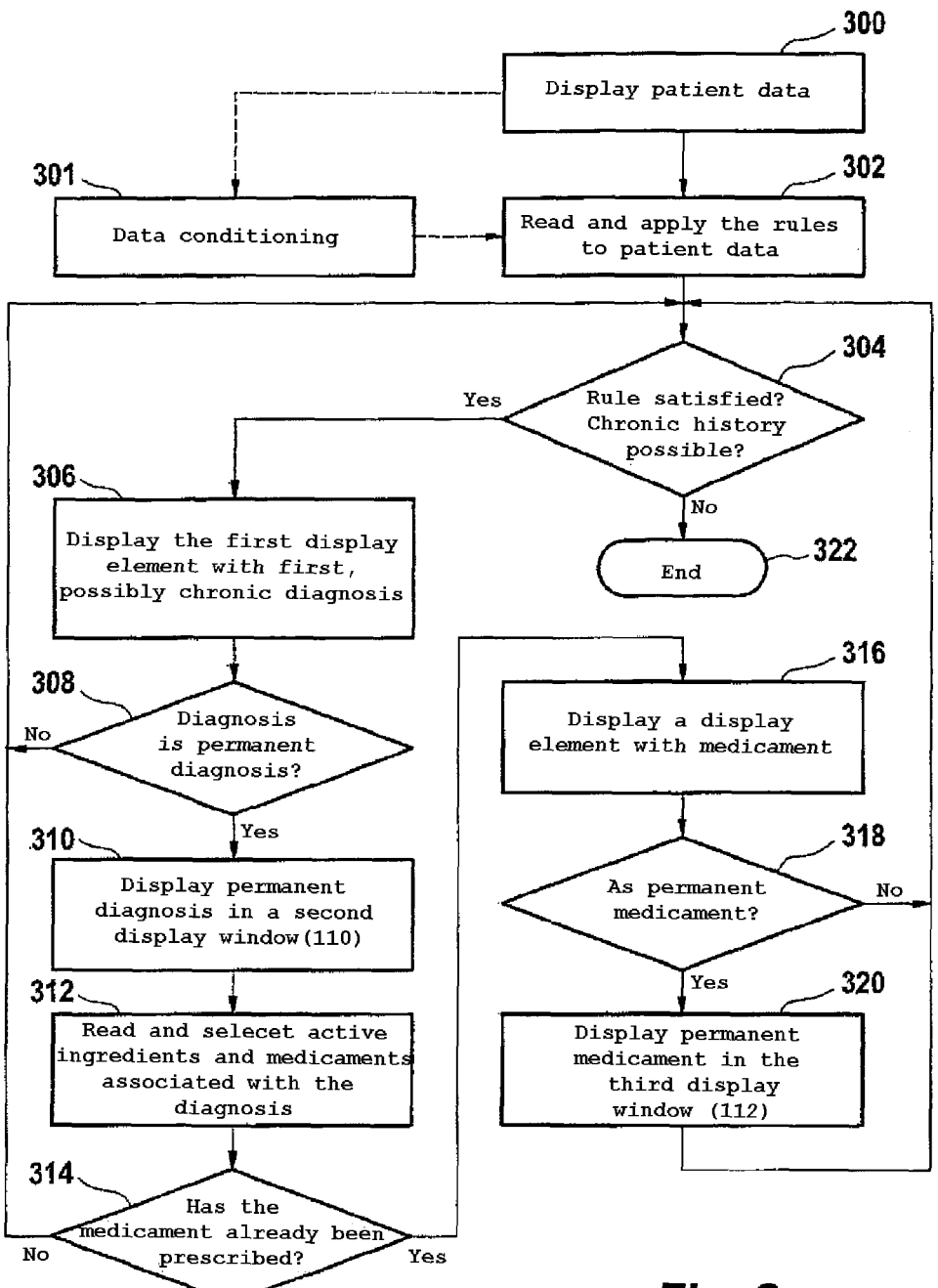
FIG. 3 shows a flowchart for a method for displaying patient-related diagnoses of chronic illnesses.

FIG. 3 shows a flowchart for a method for displaying patient-related diagnoses of chronic illnesses on a graphical user interface in a data processing system. The method starts in step 300 with the display of the patient data in a display window 114, said display window having a scrollbar and only some of the patient data being displayed in this display window. In step 302, rules are then read and applied to the patient data, said rules containing query conditions and being applied to the available patient data for a patient. The rules 128 are stored in a first database 122 in combination with medical diagnosis objects 124. The structure of the rules is shown in detail in FIG. 6. Step 302 is followed in step 304 by the check to determine whether at least one of the rules is satisfied for the patient data. If this is not the case, the method then ends in step 322. If, by contrast, one of the rules is satisfied for the patient data in step 304, the method continues in step 306 with the display of a display element on the graphical user interface, said display element having at least one of the diagnosis objects, for example an ICD code which is part of the relevant diagnosis object, for which the rule is satisfied. If the ascertained diagnosis is a possibly chronically occurring diagnosis (possible permanent diagnosis), a user query is subsequently output on the graphical user interface in step 308 regarding whether a medical diagnosis linked to the diagnosis object is intended to be accepted as a chronic permanent diagnosis. If the medical diagnosis is not intended to be accepted as a chronic permanent diagnosis, the method returns to step 304, where a check is performed to determine whether a further rule is satisfied for the patient data. Steps 304 to 308 are therefore performed cyclically for all the rules.

If the treating doctor decides in step 308 to accept the diagnosis as a permanent diagnosis, the permanent diagnosis, for example in the form of the ICD code, is displayed permanently in a second display window in step 310, regardless of the position of the scrollbar in the first display window.

Following step 310, or optionally in parallel with step 310, step 312 is executed—access to the first database 122, which stores the medical diagnosis objects with information regarding which active ingredients need to be prescribed when a diagnosis has been made. The information regarding which active ingredients need to be administered for a particular diagnosis may alternatively also be stored in a fourth database 142. If it has been possible to ascertain at least one relevant active ingredient, a further database containing medical medicament objects is accessed 312, said medical medicament objects being stored in combination with information about contained active ingredients. This step involves ascertainment of all the medicaments which contain at least one of the previously ascertained active ingredients. In step 314, a check is performed on the patient data to determine whether the previously ascertained medicaments have already been prescribed for the patient. This step may optionally also be linked to a check on the time constant for the prescription of the medicament, which can be ascertained from the patient data 134. If the medicament was prescribed a very long time ago, the medicament is in this case ignored in 314. If the medicament has not yet been prescribed or if it was prescribed too long ago, the method returns to step 304, where checking continues cyclically in steps 304, 306 and 308 to determine whether at least one of the other rules is satisfied for a chronic illness.

If condition 314 is satisfied for the patient data, however, the method continues in step 316 with the display of a display element on the graphical user interface which proposes at least one of the medicament objects to the user for selection, wherein the proposed medicament objects contain at least one active ingredient against the permanent diagnosis confirmed by the user and have already been prescribed for the patient. It is also possible to display only some of the data associated with a medicament object, such as a central pharmaceutical number or an active ingredient description or a medicament name. The query in step 318 is used to allow a doctor to decide whether he wishes to use the displayed medicament for permanent medication. If he does not, the method returns to step 304. If he does wish to use the medicament for permanent medication, however, then step 318 is followed by step 320 with display of the medicament in a third display window 112 of the graphical user interface on a permanent basis, that is to say regardless of the position of the scrollbar. Following step 320, the method again returns to step 304.

It is noted that, instead of a direct transition from step 300 to step 302, it is also possible to use an intermediate step 301 to perform data conditioning for the patient data. In this regard, those data which are structured are filtered from the patient data, for example. These structured data are then kept in an appropriate memory, for example a cache memory, denoted by the reference symbol 140 in FIG. 1.

In addition, in accordance with a further embodiment of the invention, it is possible to display to the user, as a proposal for possible permanent diagnoses, only those possible chronic diagnoses which are linked to a certain threshold value for the presence of a chronic manifestation. Mention has already been made of the possibility of actually displaying the first diagnoses, which have been ascertained by applying the rules, only if they have a diagnosis risk above a threshold value. Furthermore, the general diagnosis risk threshold value for when permanent diagnoses/chronic illnesses are predicted may have an additional value in the calculation of the risk of the presence of a chronic illness. This occurs by virtue of the medical diagnosis objects being stored in combination with a probability value which indicates the probability of a diagnosis having a chronic manifestation. There are diagnoses which are usually chronic when they occur, whereas others are normally one-off diagnoses which have a chronic manifestation only among a small minority of patients. In addition, there is also the primary risk for each diagnosis in the system or, following application of the rules, a first diagnosis risk. By virtue of the first diagnosis risk being stored in combination with the risk value, which indicates the probability with which a diagnosis has a chronic manifestation when it occurs, being multiplied, it is possible to predict the risk of the presence of a chronic diagnosis even more precisely. In accordance with this embodiment of the invention, it is possible to specify a specific threshold value for this risk, so that diagnoses are proposed to the user as possible permanent diagnoses only if the risk thereof of the presence of the chronic form of a diagnosis is above said second threshold value.

Figure 4A:
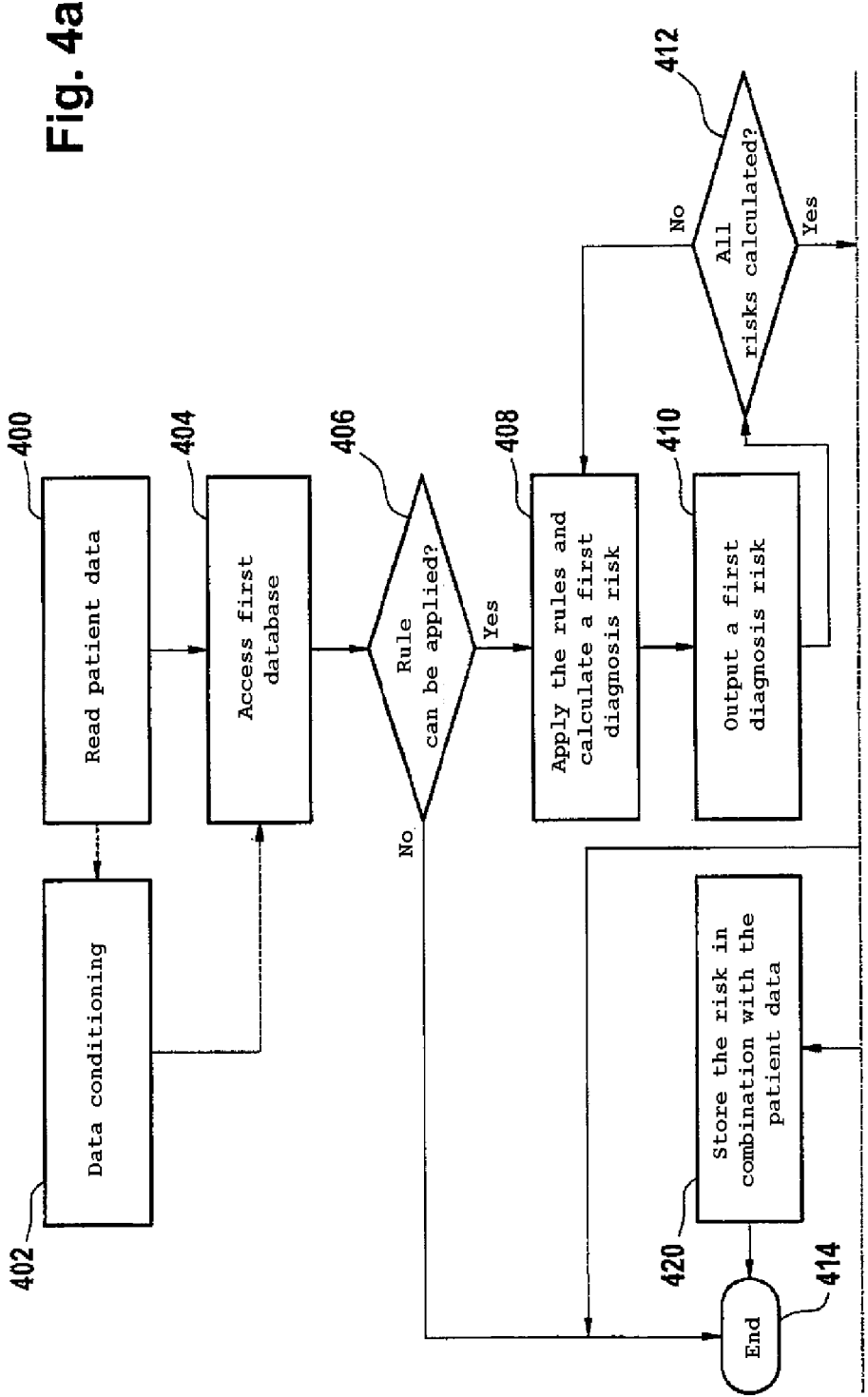
FIG. 4 shows a method for medical diagnosis assistance for patient data for a patient.
Figure 4B:
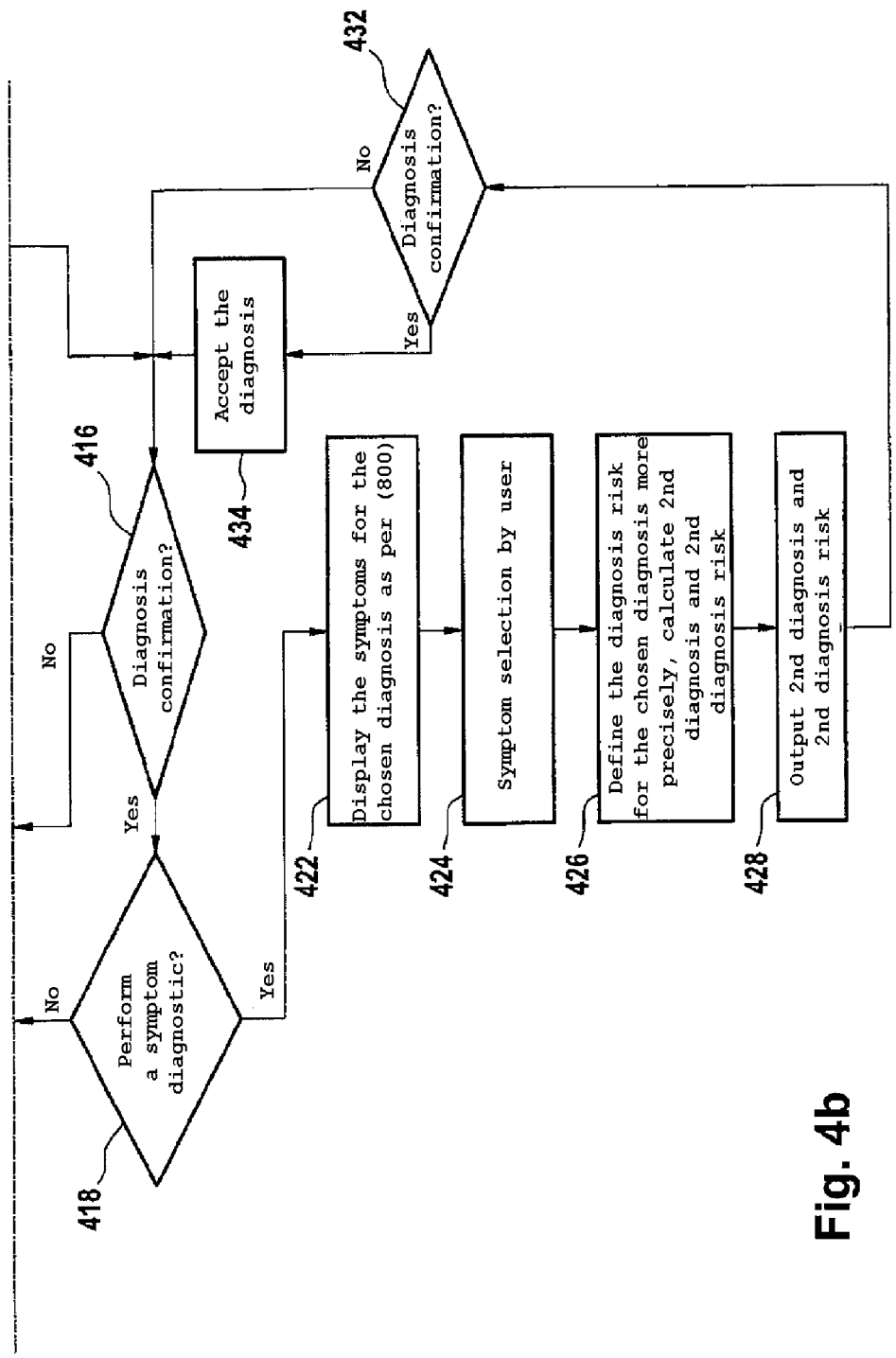
Figure 4C:
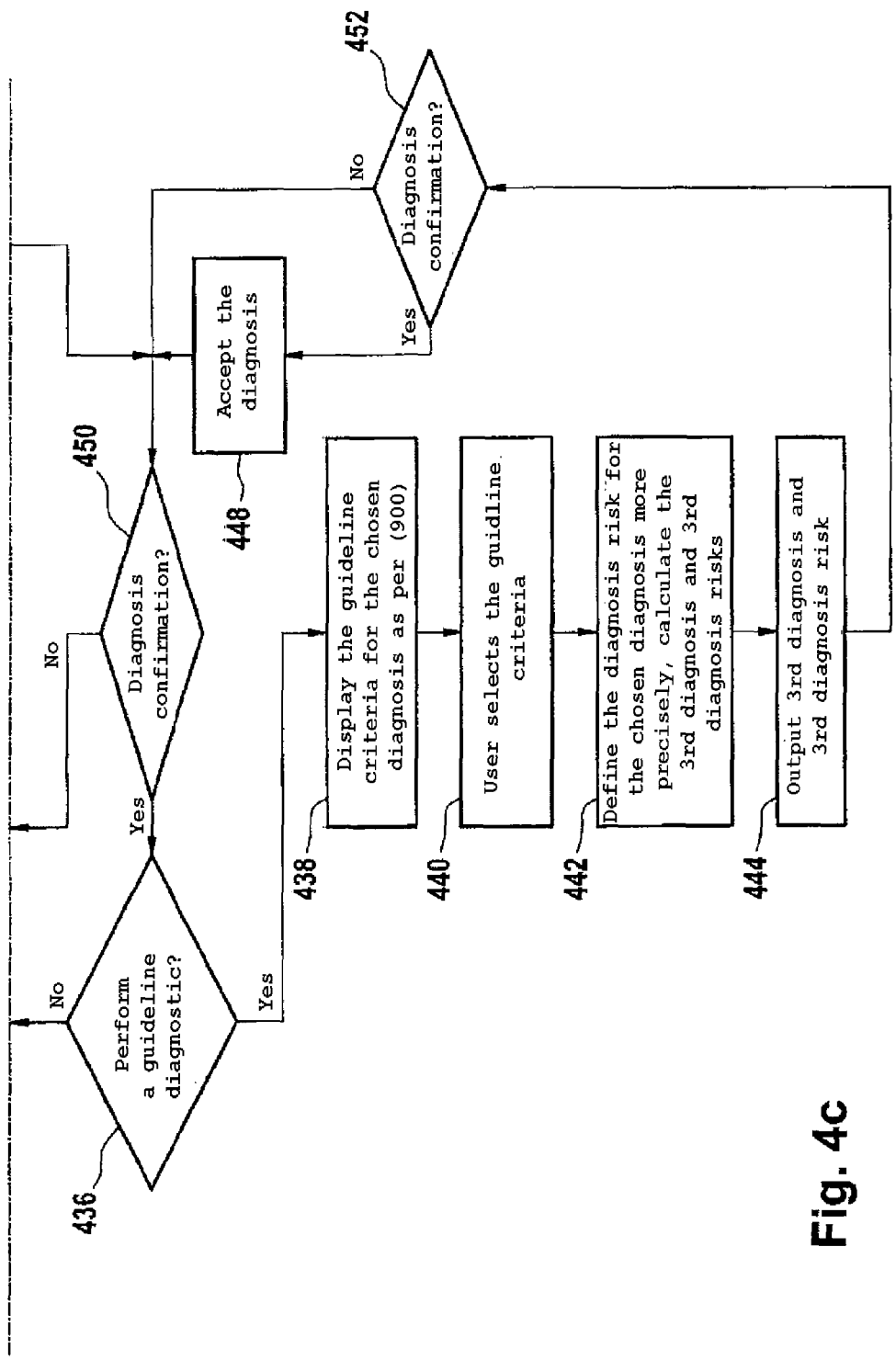
Figures 1, 5:
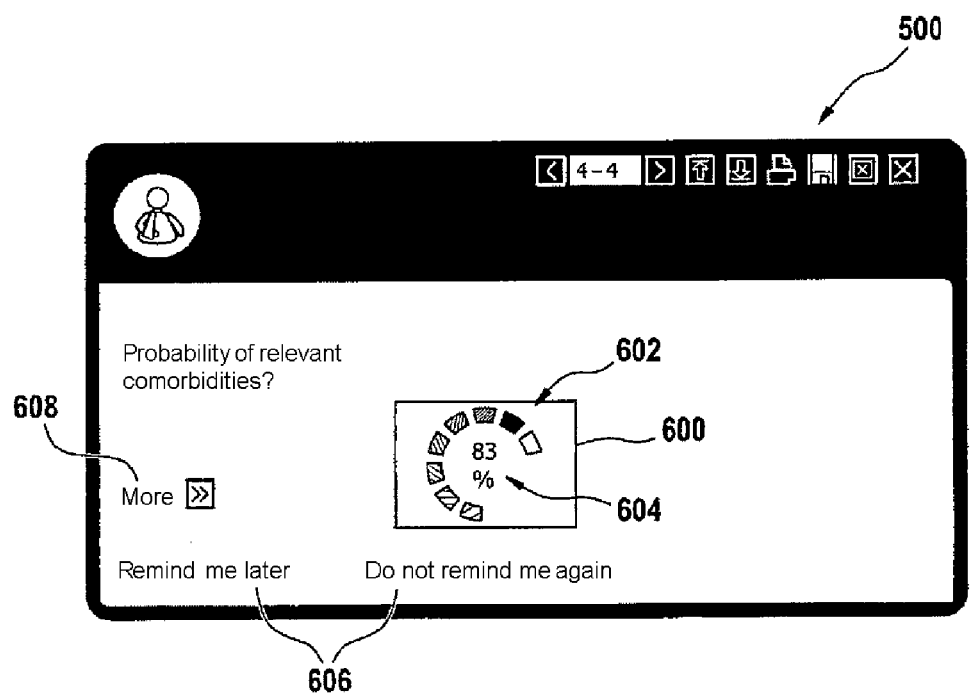
FIG. 5 shows steps in a method for medical diagnosis assistance for patient data for a patient.
Figures 3, 5:
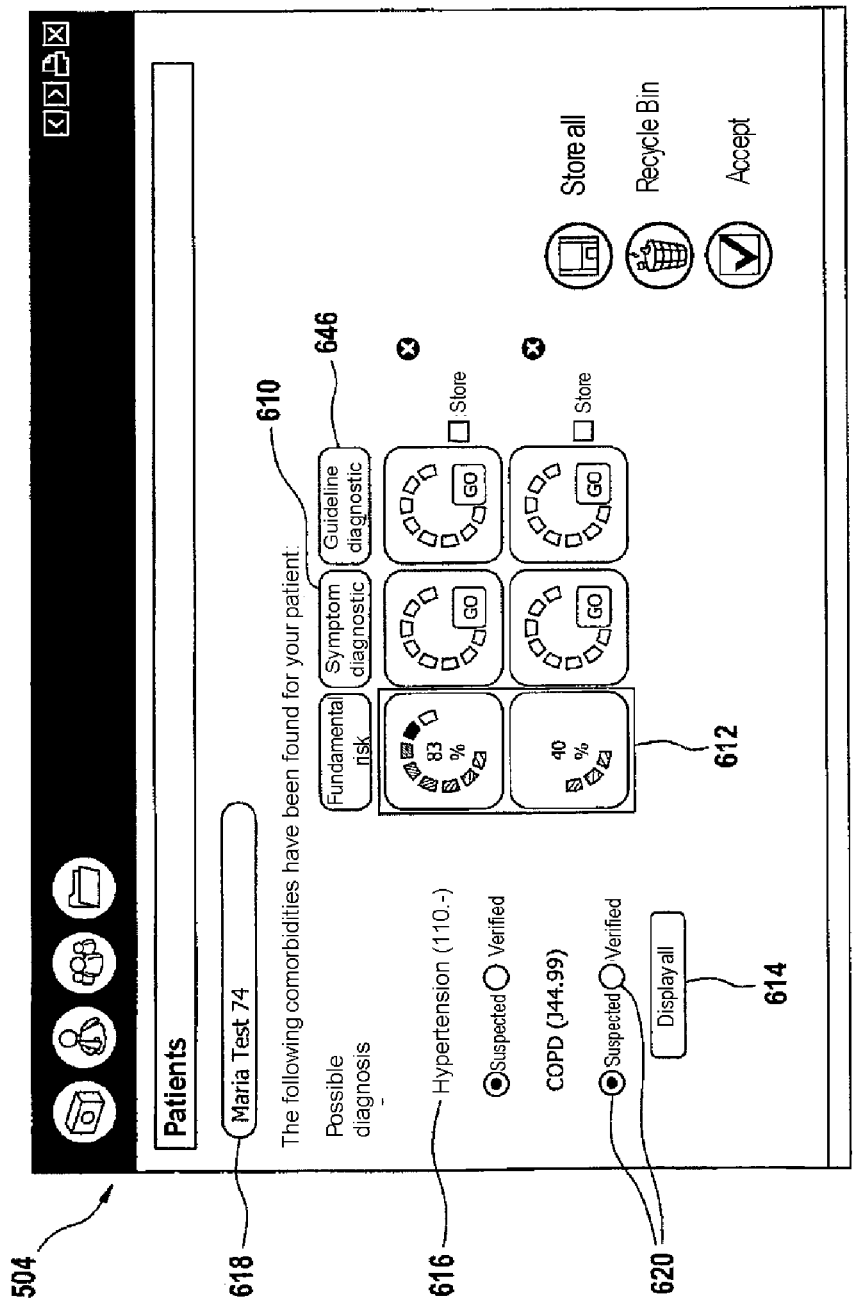
Figures 4, 5:
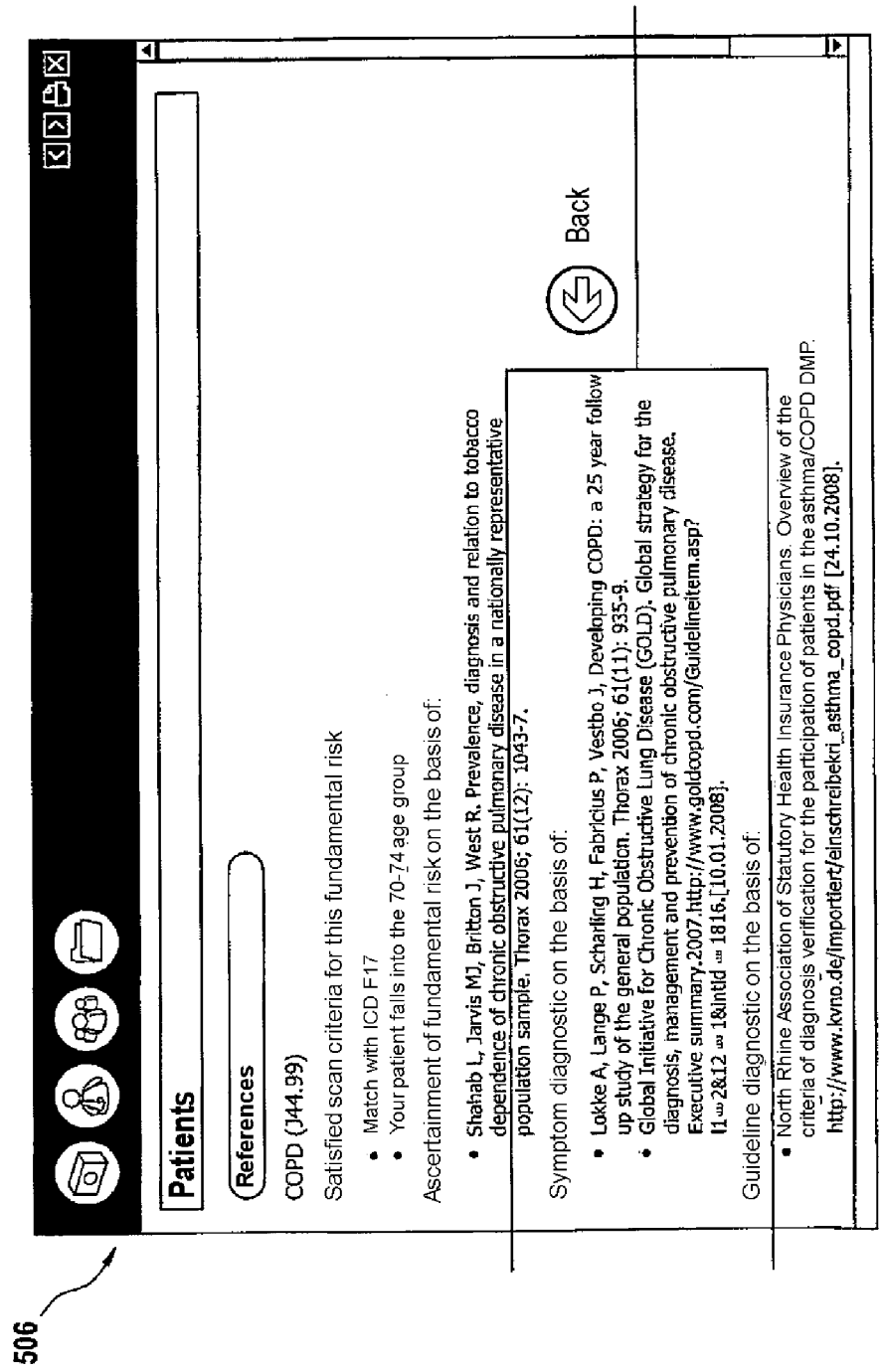
Figure 5:
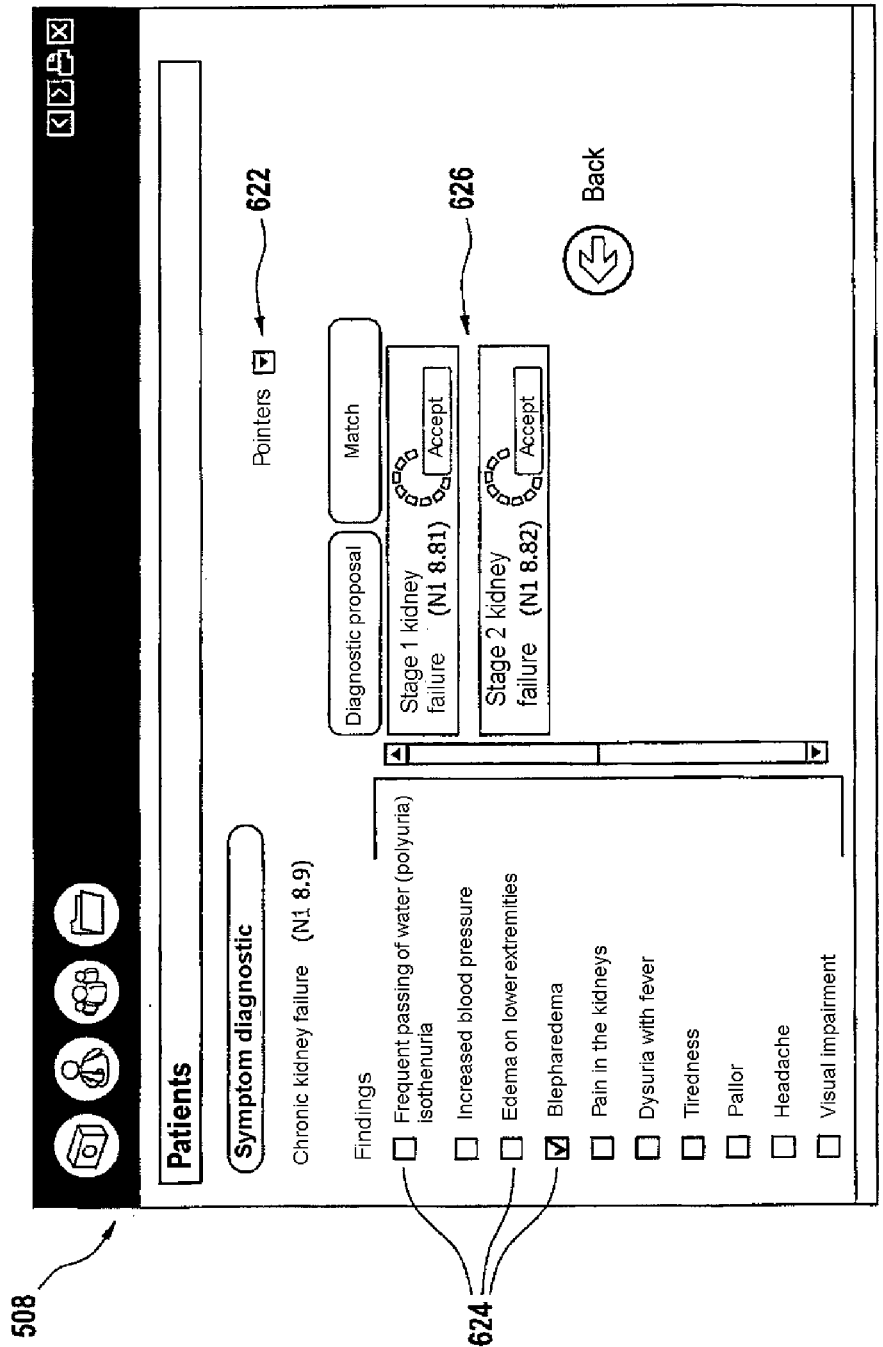

FIG. 4 shows a flowchart for a method for medical diagnosis assistance for patient data for a patient by a data processing system. In this case, FIG. 4a shows the method for calculating the first diagnoses and diagnosis risks by applying rules to the patient data. FIG. 4b shows the further more precise definition of the diagnosis risk for a previously calculated diagnosis, e.g. for a diagnosis which has been calculated in FIG. 4a, by means of symptom diagnostic. FIG. 4c shows the further more precise definition of the diagnosis risk for a previously calculated diagnosis, e.g. for a diagnosis which has been calculated in FIG. 4a or 4b, by means of guideline diagnostic. The method starts in step 400 with the reading of patient data from a database. In this case too, step 400 is again followed by the optionally available step 402 of data conditioning, with the first database being accessed either after step 402 or directly after step 400 so as to retrieve rules for calculating diagnosis risks for medical diagnoses. In step 406, the check is performed to determine whether at least one of the rules can be applied to the patient data. If this is not the case, for example because there are too few patient data available or because the available patient data are too old, then the method ends in step 414. If at least one of the rules can be applied in step 406, however, step 408 then takes place, in which the rules are applied to the patient data, as a result of which a diagnosis risk is calculated for a first medical diagnosis. This first medical diagnosis is output in step 410 together with the first diagnosis risk on the graphical user interface. Step 410 is followed in step 412 by a check to determine whether all the risks have been calculated for all the possible medical diagnoses. If this is not the case, the method again continues with steps 408 and 410, again followed by step 412.

It should be noted that FIG. 4 does not show the additional possibility of limiting output of diagnosis risks to an appropriate minimum probability, starting from which appropriate diagnosis risks are actually first output on the graphical user interface.

If step 412 reveals that all the risks have been calculated, the method continues in step 416 with the output of a user query regarding whether the diagnosis denoted by a particular risk can be accepted in the patient data as a verified diagnosis. If this is not the case for any of the calculated diagnosis results, the method ends in step 414. However, it is also possible to store one of the displayed diagnosis results directly, for example for a high diagnosis probability of above 90%, either automatically or following confirmation by the treating doctor, in combination with the patient data in the relevant patient database in step 420, whereupon the method ends in step 414 after step 420.

Alternatively, it is possible, when a diagnosis is confirmed in step 416, to provide the doctor with the option in step 418 or 436 of performing an interactive symptom diagnostic or guideline diagnostic. If the doctor does not wish to perform such analysis, step 418/436 is followed by the already mentioned step 420 of storing the diagnosis as a verified diagnosis, in combination with the patient data in the patient database. This is in turn followed by step 414 when the method is terminated.

If the doctor does wish to perform an interactive symptom diagnostic in step 418, the method continues in step 422. If the doctor wishes to perform an interactive guideline diagnostic in step 436, however, then the method continues in step 438.

In summary, steps 416 and 450 therefore serve to provide the doctor with a choice between a) direct acceptance of one of the diagnosis results as a verified diagnosis, b) rejection of all the diagnosis results or c) performance of an additional interactive symptom diagnostic or guideline diagnostic for one or more of the first diagnosis results.

If the doctor now decides in favor of alternative c) and symptom diagnostic, step 422 involves the output of a checklist with symptoms which are linked to the medical diagnosis chosen in step 418 in the first database. By way of example, this can be done by accessing the first database in step 422, the first database being queried for possible symptoms for a given and chosen medical diagnosis. The first database stores those diagnoses which correlate to particular symptoms in a statistically significant manner in combination with one another, the combination also containing information about the source of literature on which said combination is based. By way of example, FIG. 800 shows a database table storing a plurality of symptoms in combination with a particular diagnosis ID 68. These symptoms linked to the diagnosis that is to be specified in more detail are then transmitted to the data processing system or are retrieved therefrom and in step 422 are displayed to the user in the form of a checklist. In step 424, the user can now select one or more of the symptoms or alternatively can also specify further details relating to symptoms, for example in the form of numerical inputs. If a symptom is "high blood pressure", for example, then the doctor can define this more precisely by additionally inputting an appropriate blood pressure value for this symptom.

The link between symptoms and correlating diagnoses is thus firstly used, as described previously, in order to set up the query elements, e.g. checkboxes, dynamically from the database for the system diagnostic for a specific symptom. Alternatively, the link is used to find further diagnoses 628, on the basis of the current symptom selection of the user 642, which correlate to the respective symptom selection. Whenever one of the symptoms has been selected or defined more precisely, an updated calculation of the diagnosis risk for the currently chosen diagnosis is performed dynamically by applying the symptom diagnostic rules 800 to the previously determined diagnosis risk. In addition, it is also possible to output further medical diagnoses with associated diagnosis risks which correlate to the selected symptoms. The correlation between the chosen symptoms and the diagnoses is, as already mentioned previously, literature-based and stored in the first database.

In accordance with a further embodiment of the invention, the additional diagnoses can be accepted by the user in the list of first diagnoses (suspected diagnoses hypertension and CPOD in FIG. 5-1 are complemented, for example after the symptom diagnosis, by the suspected diagnosis of stage II kidney failure by virtue of selection by the user). The calculation of a second diagnosis and of a second diagnosis risk which is mentioned in 428 is likewise effected by applying the symptom diagnostic rules in table 800 and can, as presented in the display window 510, by all means contain a plurality of second diagnoses, correlating to the symptom selection, with second diagnosis risks. For the sake of simplicity, 426 in FIG. 4b shows only a single second diagnosis and 442 in FIG. 4c shows only a single third diagnosis. However, figure element 630 shows that it is also possible for a plurality of diagnoses to correlate to the first diagnosis.

This application of the rules 408 taking account of the patient data and also the additionally more precisely defined symptoms by the user and the corresponding fresh calculation of the diagnosis risk take place in step 426. The diagnosis risk is output together with the additional determined medical diagnoses in step 428.

Step 426 contains the following substeps: when the symptom diagnostic has been selected in order to define even more precisely the risk of a stroke in a patient of 55%, as obtained using the rules, the course of the symptom diagnostic thus first of all involves all the symptoms which are stored with the ID of the stroke diagnosis within a row being read from the table 800. A data entry with the diagnosis ID for stroke thus corresponds to a selection element, e.g. a checkbox. If stroke has the associated ID 444, the symptom diagnosis query window contains two three selection elements with the symptoms of the symptom IDs 1324 and 1325. If the user selects the symptom 1324, the predetermined risk of stroke for the patient of 55% is increased to 1.2×55%=66%. Furthermore, correlating diagnoses are displayed 628 for all symptoms selected by the user, as also shown in 624, for example. For the sake of simplicity, FIG. 4b assumes only one further diagnosis, which is also referred to as a second diagnosis with a second risk. In this case, the risk of the second diagnosis is calculated in similar fashion from the first risk—ascertained by the rules 128—of said second diagnosis, this has been additionally modulated by the current symptom selection as per table 800.

When the doctor has input relevant symptoms in step 424 and one or more second medical diagnoses and diagnosis risks have been displayed in steps 426 and 428, the doctor is provided with the opportunity in step 432 to confirm a diagnosis which has been output in connection with a diagnosis risk in step 428. If the doctor does not confirm any of the diagnoses in step 432, i.e. if he rejects all of the proposed diagnoses, then step 432 is followed by step 416, which is again used to display to the doctor the original display window in which the diagnosis risks calculated in steps 408 to 412 for various diagnoses are displayed. If, by contrast, the doctor does confirm one of the diagnoses output in step 428; 630 in step 432, this diagnosis is accepted in step 434, and is now made available to the doctor, together with the further diagnoses calculated in steps 408 to 412 and the diagnosis risks therefor, in a more precisely defined manner in step 416 for the purpose of selection for a memory in combination with the patient data, with a further interactive symptom diagnostic or else with complete rejection of all calculated diagnosis risks.

It should be noted that, instead of performing steps 400 and 404, an intermediate step 402 may also follow step 400, in which the patient data can be subjected to data conditioning.

The further more precise definition of the diagnosis risk by the guideline diagnostic in FIG. 4c and the calculation of a third diagnosis risk are effected in similar fashion to the symptom diagnostic which is shown in FIG. 4b. If the user wishes to perform a guideline diagnostic 436, those guideline criteria which are stored in combination with the diagnosis chosen by the user in the first database are displayed 438. Some or all of these guideline criteria can be selected 440 by the user. Guideline criteria which arise in a manner correlated to the diagnosis objects are likewise stored in the first database in combination with the diagnosis objects. By taking account 442 of the effects which each guideline criterion has on the previously determined diagnosis risk, and by executing guideline routines, the diagnosis risk is defined more precisely and a third diagnosis with an associated diagnosis risk is output 444; 644. This may also involve a plurality of third diagnoses and associated diagnosis risks; FIG. 4c assumes a third diagnosis risk for the sake of simplicity.

Figures 5, 6:
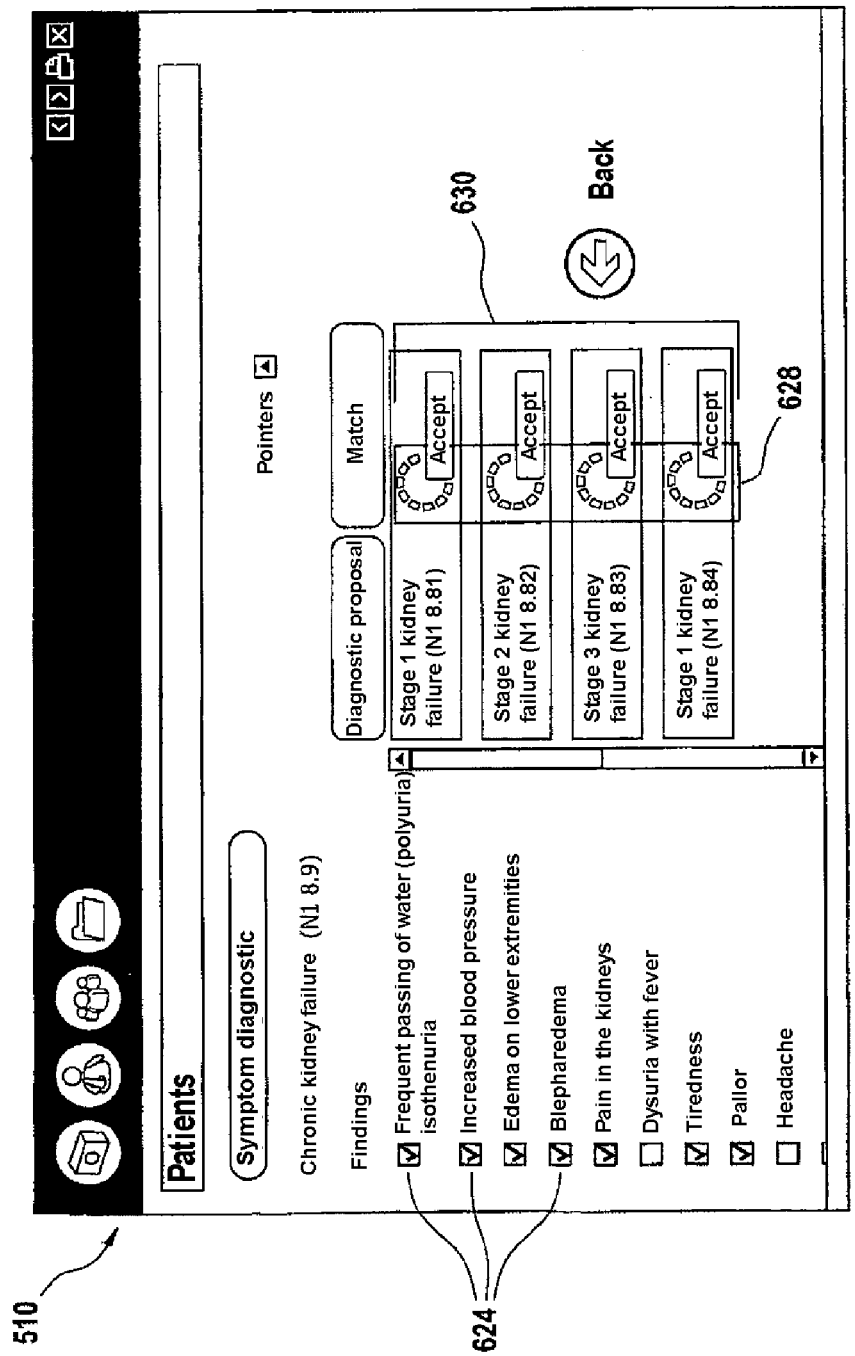
FIG. 6 shows a database table with rules for calculating the first diagnosis risks.
Figures 5, 6, 7:
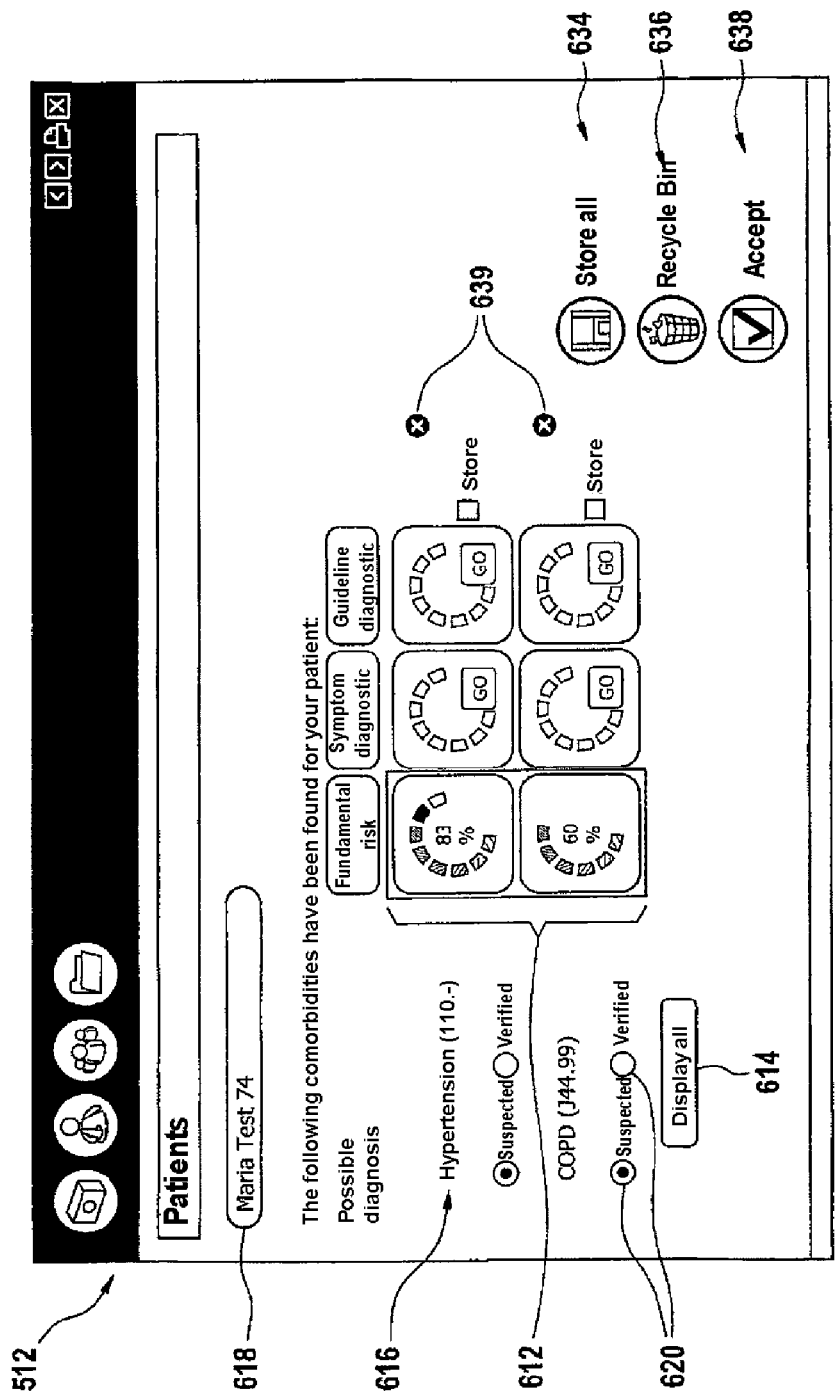
FIG. 7 shows a database table for symptom diagnostics.
Figures 5, 6, 7, 8:
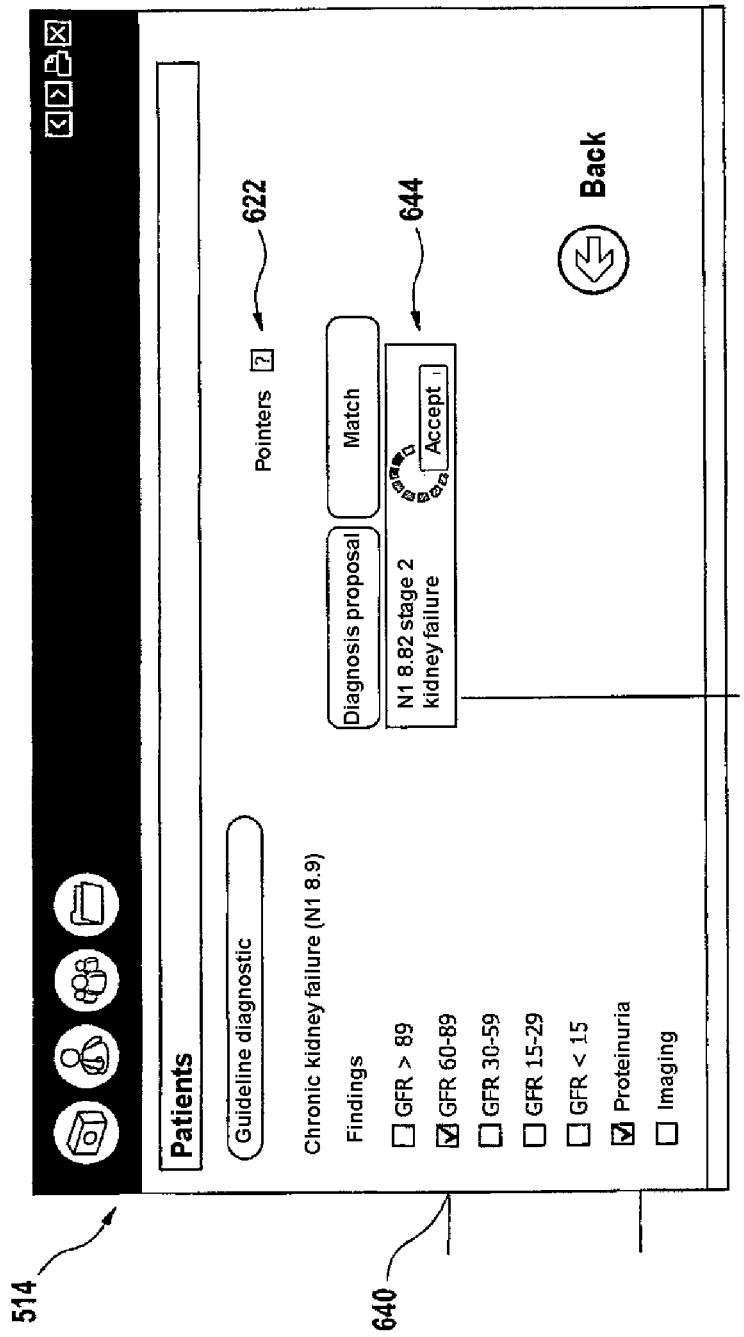
FIG. 8 shows a database table for guideline diagnostics.

The more precise definition of the previously calculated diagnosis risk in steps 426 and 442 is explained for the precise implementation of these steps in the description of FIGS. 7 and 8.

FIG. 5 shows various outputs on a graphical user interface for the situation in which medical diagnosis assistance for patient data for a patient is performed by the data processing system. This has therefore been preceded by an appropriate patient having been selected by the treating doctor and hence the patient data having been made available to the data processing system. The data processing system then analyzes the patient data automatically and, as shown from FIG. 4, applies rules to the patient data in order to calculate at least one first diagnosis risk for a first medical diagnosis.

On the basis of the health profile of the patient, i.e. the patient data which is stored as structured data in the individual patient record on the computer of the doctor (including age, sex, ICD diagnoses, prescribed medicaments, laboratory values, stored findings and symptoms), the data processing system ascertains the probability or relative frequencies of relevant comorbidities or frequently coexisting illnesses on a transparent guideline and literature basis, aligns then with the already known diagnoses and displays the previously unlisted or recognized illnesses to the doctor on an individualized patient basis, organized according to probability.

The basis used is a list of selected medical literature which has demonstrated statistical links between the existing known data, findings and illnesses and is now used for patient-individualized risk calculation. Hence, a first "diagnosis risk" is displayed to the doctor. The threshold value from which this display is intended to take effect is freely scalable.

The screen output 500 shows such output of a diagnosis risk in the form of a "tachograph disk" 602. Probabilities and/or relative frequencies can thus be visualized equally well. The tachograph disk comprises a scale with color shades, the tachograph disk preferably having red scale components for high probability, yellow scale components for average probability and green scale components for low probability. This scale in the form of traffic lights therefore enables a treating doctor to quickly and easily get a visual grasp of the probability of a relevant comorbidity. In addition, in order to define an appropriate probability of a diagnosis risk more precisely, the center of the tachograph disk indicates the primary risk in the form of a percentage probability 604 or a percentage relative frequency 604. The display element 500 thus shows the diagnosis risk by virtue of the arrangement 600 in the form of a tachograph disk and a numerical value.

In addition, the doctor is provided with the opportunity to hide the display 500 for a certain period by operating the "remind me later" button 606, or else to completely hide the display 500 of the probability of relevant comorbidities by operating the "do not remind me again" button.

The display element 500 is thus used for the purpose of clearly and generally informing the doctor about whether or not there is actually a particular diagnosis risk for a relevant medical diagnosis. A more precise definition of what this medical diagnosis looks like or whether there are several possible relevant medical diagnoses is not provided by the display element 500.

The criteria for ascertaining a particular probability are presented transparently to the doctor—upon request—on the basis of indication, as shown in display element 502. This display is provided inclusive of the sources of literature and study that are used, as a basis for the respective diagnosis method (application of the rules for determining the first diagnosis risk, symptom diagnostic and guideline diagnostic).

If the doctor now wishes to obtain further information regarding possible relevant comorbidities on the basis of the display 500, the doctor operates the "more" button 608 and thus arrives at the display element 504, which holds a summary of the comorbidities which are possible for the patient named "Maria Test 74" (reference symbol 618). Thus, the display window 504 shows the possible first diagnosis in the form of a text description together with the respective ICD 10 code (reference symbol 16), together with the respective first diagnosis risk in the form of a tachograph disk (reference sign 612). The first diagnosis or the first diagnoses are referred to as basic risk in the display 504 and subsequent displays. In addition, the doctor is provided with the opportunity to use the selection elements 620 to stipulate whether these displayed possible diagnoses individually represent just a suspected diagnosis or a verified diagnosis. The diagnosis can be stored individually, or else all the diagnoses can be stored at once, i.e. can be transferred to the patient record.

The "display all" button 614 is used to display further possible diagnoses for which the diagnosis risk is below a predetermined threshold value. In the present case, the threshold value is 40%, for example, which means that in this case only possible diagnoses which have a diagnosis risk ≥40% are displayed.

If the doctor wishes to follow up the respective diagnosis risk, he can call up the indication-related, in each case literature-based symptoms and have them aligned with findings for the patient or complement these by means of a checklist. This is done by virtue of the doctor clicking on the relevant "GO" button in column 610 so as to perform a symptom diagnostic for the respective possible diagnosis. For this too, the sources of the symptom diagnostic are respectively stored and transparently depicted for the doctor, as illustrated by display element 506. Findings already stored in structured form in the system are detected and "preselected" in another color coding. If the doctor moves the mouse over a display marked in this manner, he is shown a text with the dedicated file source (for example free-text input "consultation dated Nov. 1, 2008" or "laboratory value dated Oct. 15, 2007"). If, by contrast, the doctor clicks on the relevant "GO" button in column 646, a guideline diagnostic is performed for the respective possible diagnosis.

By operating the "GO" button in the display element 504, column 610, the doctor first of all reaches the display element 508 for the symptom diagnostic. The display element 508 has a button 622 which the doctor uses to reach the display element 506. Furthermore, the display element 622 has a checklist 624 with various symptoms (findings) which are symptomatic of the possible diagnosis 616 for which the relevant "GO" button has been chosen in display element 504. Thus, display element 508 is used to display a diagnosis proposal 626 for the chosen symptoms together with an appropriate match in the form of a freshly calculated diagnosis risk as a tachograph disk. As illustrated by the display element 510, for example, every further selection of one of the check elements prompts the diagnosis proposal and the corresponding match to be updated, which in turn results in an arrangement 628 of diagnosis risks which is sorted according to probabilities. As can clearly be seen from the relationship between the display element 508 and the display element 510, the diagnosis proposal made first of all is furthermore defined more precisely in dynamic fashion by virtue of the selection of further findings. The display element 508 was thus merely able to be used to determine the possible presence of stage I or stage II kidney failure, whereas the display element 510 was able to be used to perform a fresh calculation of diagnosis risks for various medical diagnoses on account of a more accurate more precise definition of the available findings, suitable additional diagnoses now being stage III and stage IV kidney failure. Furthermore, the probabilities were presented on the basis of more precisely defined calculation in the form of the tachograph disks 628 in the display element 510.

In summary, the treating doctor can add the display elements 508 and 510 to the necessary symptoms/findings—by consulting the patient, examination or the addition of already known information to the checklist. Depending on the symptom situation, this gives rise to those diagnosis proposals together with ICD 10 codes, i.e. in plain text and coding, which, according to the specified literature, i.e. corresponding symptom diagnostic rules, correlate to the described finding. In addition, the display is converted dynamically, i.e. the filling level for the tachograph disk already described and insertion of the plausible ICD diagnoses, depending on further findings and level of correlation.

As can also be seen from display element 510, the respective diagnosis proposal can be accepted directly into the central overview, the process being able to be performed with one or else more diagnoses. A central overview which has been more precisely defined in this manner is shown by means of display element 512. The display element 512 in turn shows the name of the patient 618 and also the possible diagnoses 616.

Comparing the display element 512 with the display element 504, it can be seen that performance of a symptom diagnostic has increased the diagnosis risk for the diagnosis COPD (J44.99) from 40% to 60%.

The central overview now allows the doctor to have all the comorbidity probabilities displayed (button 614) and to reject relevant diagnoses (click on the cross 639, and possibly reactivate later) or else to store all displays (click on element 634). It is also possible to reject all the diagnoses at once (click on element 636), or all the diagnoses and displays can be accepted by clicking on the element 638. In the latter case, the possible diagnoses and symptoms are not transferred to the patient database, but rather the system merely remembers the view 512, so that the doctor can restore this view identically at a later time.

A further alternative is to allow the "suspicion" preselection 620 to exist until a threshold value probability, which is preferably very high (above 90%), is exceeded. From this moment onward, the selection is automatically changed to "verified".

In addition or as an alternative to the interactive symptom diagnostic, the doctor is able to display and go through the respectively proposed guideline diagnostic in order to finally verify the diagnosis. An appropriate display window is provided by the display element 514. Selecting the box 622 in turn opens a display window 516 which names the relevant guideline diagnostic for corresponding literature sources for the necessary or recommended diagnostic and also the interpretation thereof. The display element 514 is used to display respective correlating indications and to provide them with a graphical degree of correlation again. The most plausible diagnosis (or another one) can be accepted directly into the overview and subsequently into the file.

FIGS. 6, 7 and 8 show a simplified form of the database tables on which the individual risk calculation methods are essentially based in accordance with one preferred embodiment of the invention.

Database table 700 in FIG. 6 contains the rules 128 which are applied directly when the patient record is opened in order to calculate the first diagnosis risks. Each rule has an ID (column 702), a value which specifies how greatly the primary risk changes if the rule can be applied to a patient (column 716), and a diagnosis which is associated with the rule and which is identified by means of a diagnosis ID (column 716) in the table 700. Furthermore, the table contains further columns containing conditions for the rule to pertain, that is to say by way of example the medication which the patient has taken to date (column 704), ICD codes (column 706), LEZ codes (column 708), the age (column 710) and the sex (column 712) of the patient. The list is not conclusive, the aforementioned database table 700 is based on a preferred embodiment of the invention, and further embodiments with additional or occasionally differing features are possible.

Not every feature usually also needs to have a data value provided for it (by way of example, rule 1988 has no value for an ICD code). A particular diagnosis, e.g. the diagnosis for the ID 23, may have a plurality of associated rules (rule IDs 1987-1989). If a rule can be applied to a patient, this modifies the primary risk in the patient for the presence of a particular diagnosis. If rule ID 1987 applies to a patient, for example, this increases his risk of diagnosis with ID 23 by 15.23%. The diagnosis risks (column 716) may also be provided with relative values, e.g. "x 1.2". Such values can be understood to mean that the diagnosis risk when the rule can be applied is calculated by multiplying the primary risk of the diagnosis related to the rule by the factor 1.2. A rule can be applied if all the conditions in the individual columns are satisfied. Rule 1987 can thus be applied and modifies the level of diagnosis risk for diagnosis with ID 32 if the patient is male, is between 35 and 45 years old and if the electronic patient record for the patient already contains a note of the ICD code 706 and the LEZ code 54. Whether the patient is taking particular medicaments is usually disregarded.

By applying all the rules from 700 to the patient data which the patient record contains when the latter is opened, it is thus already possible to calculate a large number of first diagnosis risks which differs significantly from the respective associated statistical primary risk. As a result of the diagnoses which are above a certain threshold value being displayed to the doctor, the latter can use the short time available to him for analyzing the patient's medical history very efficiently. Since the system already takes away from the doctor and automates many steps in diagnosis and patient history, the doctor now need essentially only confirm, reject or possibly define even more precisely the proposed diagnoses, in which case he can again resort to the assistance of the diagnosis method according to the invention.

In accordance with a further embodiment of the invention, the rules for each diagnosis are applied to the patient data in a manner organized according to the level of their effect on the primary risk. As soon as a diagnosis is correct, the application of the rules for this diagnosis is terminated. The background to this is that if the rules are implemented in a manner organized according to the level of the value in column 716 and, by way of example, rule 990 is correct for the diagnosis 23, there is no longer any advantage in implementing rules 1987 and 1988, since these would have a relatively small effect on the primary risk.

FIG. 7 shows a detail from a simplified database table according to a preferred embodiment of the invention which is used for symptom diagnostics. In table 800, which contains symptom diagnostic rules for defining the diagnosis risk even more precisely, one or more symptoms are associated by means of the symptom IDs 802 thereof with a diagnosis by means of the diagnosis ID thereof. In the example shown, diagnosis ID 68 has a plurality of associated symptoms (ID 1321-1323). If the diagnosis method according to the invention has established a diagnosis risk for a particular illness, e.g. a risk of 60% for diagnosis with ID 68, when a patient record has been opened and if the user has chosen to perform an interactive symptom diagnostic, the user is first of all presented with a selection of symptoms which are associated with the first diagnosis. In the example shown, the descriptions of all the symptoms which are linked to the diagnosis ID 68 according to table 800 would be proposed to the user for selection. The entries (rows) in the table 800 thus each correspond to a graphical selection option for the doctor on a display. In accordance with one embodiment of the invention, the selection option is implemented in the form of a checkbox. This means that the user would be presented with the description 804 of the symptoms 1321-1323 in the form of checkbox elements of a graphical user interface if he has previously selected the performance of an interactive symptom diagnostic in order to define the diagnosis risk for the diagnosis 68 even more precisely. As a result of some of the presented symptoms being selected or deselected by the user, the first diagnosis risk—which is the starting value for the symptom diagnostic—is modified. The result of this modification is a second, more precise diagnosis risk. Selection of the symptom with the ID 1322 increases the first diagnosis risk by 12.9%, for example. Selection of the symptom with the ID 1324, on the other hand, multiplies the first diagnosis risk by the factor 1.22. Symptom diagnostic rules thus serve to define the previously determined diagnosis risk even more precisely by factoring in the presence of particular symptoms.

FIG. 8 shows a detail from a simplified database table in accordance with a preferred embodiment of the invention which is used for guideline diagnostics. In table 900, one or more symptoms and laboratory findings, denoted as guideline criteria, with guideline criterion IDs 902 are associated with a diagnosis ID. Diagnosis ID 68 is thus associated with the guideline criterion IDs 1421-23. In the course of more precise definition of an existing diagnosis risk for the diagnosis 68 by a guideline diagnostic, the user would be shown those guideline criteria 1421-1423 on a graphical interface which are linked to one another as per database table 900. By applying these guideline routines, the precision of the diagnosis can be improved still further, and the ascertained new diagnosis risk is returned as third diagnosis risk. In a similar manner to the symptom diagnostic, the user is able to select or deselect individual guideline criteria in order to define diagnosis risks even more precisely. Furthermore, the guideline diagnostic involves the opportunity to formulate guideline routines (values from column 904 for the entries ID 1426-1430) specifically for a diagnosis for which the risk needs to be defined more precisely. By way of example, these guideline routines may contain complex Boolean or arithmetic functions which are applied to the data which the user provides by selecting relevant guideline elements on a graphical interface. By way of example, a guideline routine could query the presence of two particular guideline criteria while a particular laboratory value is simultaneously available and, if the query conditions pertain, could appropriately modify the risk—calculated up to that time—of the diagnosis for which the guideline diagnostic is performed. The laboratory value could be applied to the diagnosis risk as a multiplication factor, for example, if the level of risk correlates directly to the laboratory value. The guideline routine thus checks whether the required guideline criteria situation obtains and prompts appropriate modification of the previously known diagnosis risk in accordance with a computation routine which is contained in the code of these guideline routines and therefore does not appear in the database table. As a result of the guideline routine being able to be adapted specifically for each diagnosis without having to change the database scheme, a high level of complexity arises for the calculation of the diagnosis risk. In a similar manner to the symptom diagnosis table 800, table 900 thus contains guideline criteria which are used to define the previously determined diagnosis risk even more precisely by factoring in the presence of particular guideline criteria. Unlike in the case of the symptom diagnostic, the guideline diagnostic table 900 additionally contains diagnosis-specific guideline routines.

Figures 5, 6, 7, 8, 9:
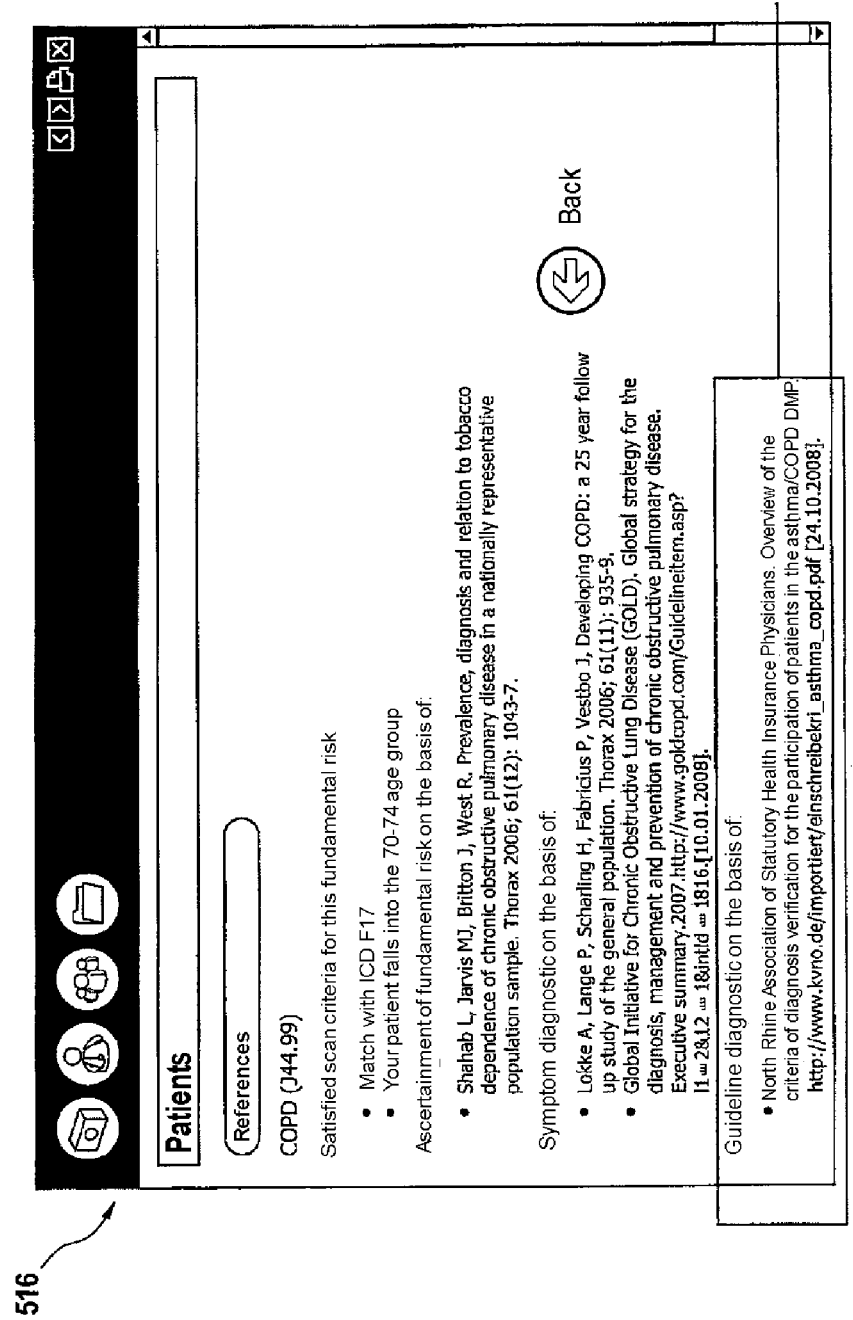
FIG. 9 shows a computer-readable storage medium.
Figure 9:
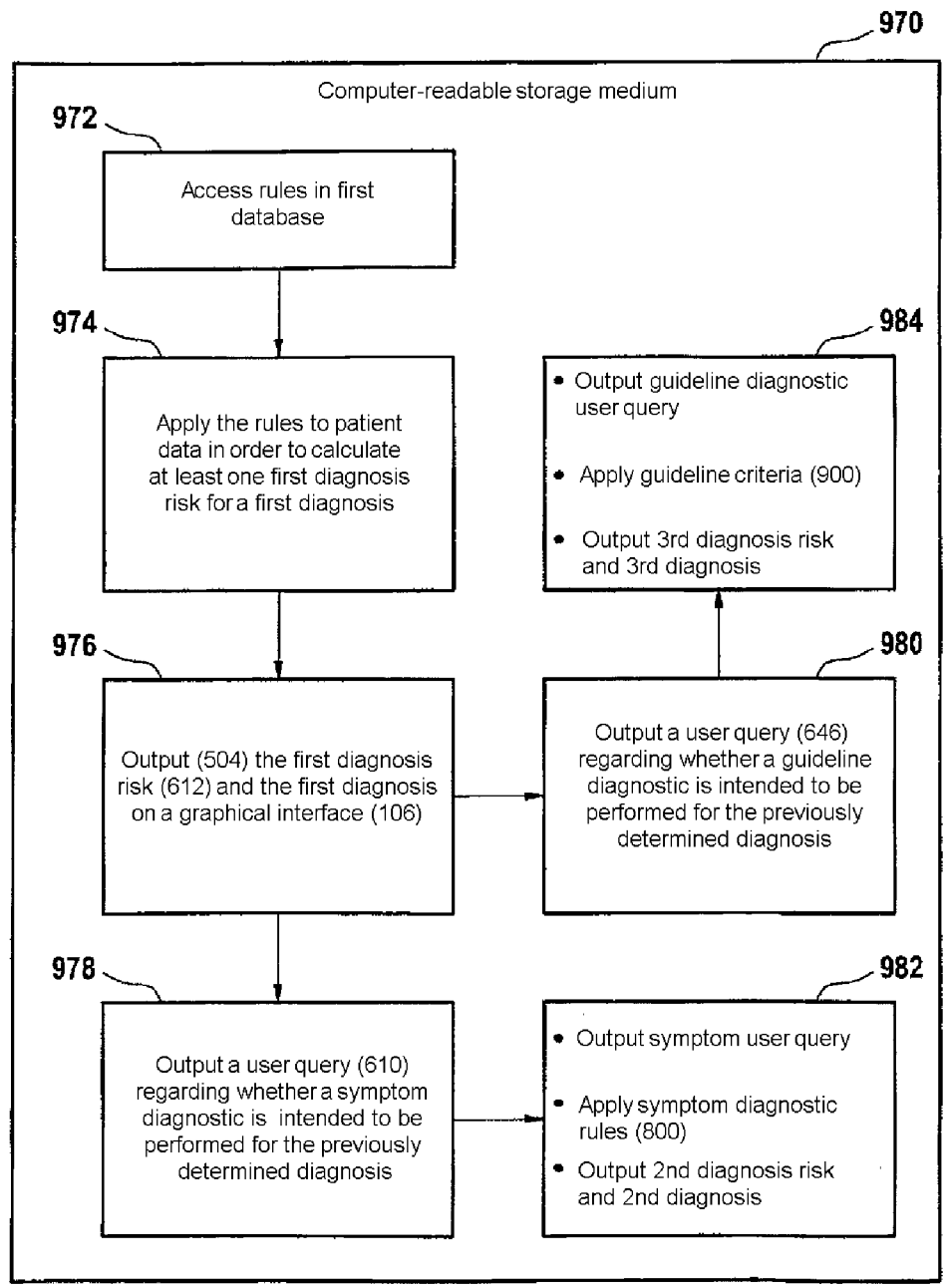

The embodiment of the invention which is shown in FIG. 9 uses JavaScript code in order to implement the guideline routines in the browser of a user. Other embodiments of the invention can use any other programming languages for implementing the guideline routines, however.

It should be noted that where relevant chronic illnesses are present and a permanent medication has been selected by the doctor, it is also possible to output a further display element which displays the time range for the two most recently prescribed pack sizes in relation to the preselected standard dosage, organized according to organ system, for example in parallel with the opening of a prescription form. Once the doctor has filled in an electronic prescription plan, these data are used as a basis for calculation. Furthermore, the doctor is also able to input the current dosage directly and hence to resharpen calculation of time ranges.

A further option is for guideline substances to be proposed according to organ systems when a guideline diagnostic, as described in display element 514 in FIG. 5, is performed. This extends the function of the display of a time range for medicament packages by the manifestation that—when chronic illnesses are in evidence—guideline diagnostics are accessible—when recommended active ingredients have not been prescribed—despite indication provided on literature basis—, organized according to organ systems, the doctor can be shown the recommended indicator substances in order to ensure that the patient is supplied adequately.

LIST OF REFERENCE SYMBOLS

100 Data processing system
102 Input means
104 Processor
106 Graphical user interface
108 Display apparatus
110-114 Display window
116 Memory
118 Network
120 Interface
122 Database
124 Medical diagnosis object
128 Rules
130 Symptoms
132 Database
134 Patient data
136 Medical medicament object
138 Active ingredient data
140 Cache
142 Database
144 Server
200 Scrollbar
202 Element
204 Element
206 Popup
300-444 Method steps and conditions
500-516 Display element
600 Arrangement
602 Tachograph disk
604 Probability
606 Input area
608 Input area
610 Symptom diagnostic
612 Fundamental risks/first diagnosis risks
614 Operator control element
616 Diagnosis
618 Patient name
620 Radio button
622 Operator control element
624 Checkbox
626 Diagnosis proposal from symptom diagnostic
628 Diagnosis risks from symptom diagnostic
630 Button
634 Button
636 Button
638 Button
639 Button
640 Findings/guideline criteria from guideline diagnostic
644 Diagnosis proposal from guideline diagnostic
646 Guideline diagnostic
648 Diagnosis risks from guideline diagnostic
700 Database table for calculating first diagnosis risk
702 Rule ID table column
704 Medication table column
706 ICD table column
708 LEZ table column
710 Age table column
712 Sex table column
714 Diagnosis ID table column
716 Effect on primary risk
800 Database table for symptom diagnostic
802 Symptom ID table column
804 Description table column 806 Diagnosis ID table column
808 Effect on previously calculated diagnosis risk table col.
900 Database table for guideline diagnostic
902 Guideline criterion ID
904 Description/guideline routine table column
906 Diagnosis ID table column
910 Effect on previously calculated diagnosis risk table col.
970 Computer-readable storage medium
972-984 Instructions for performing a computer-implemented method

The invention claimed is:

1. A computer-implemented method for medical diagnosis assistance for patient data for a patient by a data processing system utilizing a processor, wherein the data processing system has a graphical user interface and performs the following steps:
accessing a first database, wherein the first database contains rules, wherein the rules are designed for calculating diagnosis risks for medical diagnoses, wherein the first database also stores the medical diagnoses in combination with medical symptoms,
applying the rules to the patient data and calculating at least one first diagnosis risk for a first medical diagnosis based on a determination that at least one of the rules can be applied to the patient data,
outputting the first diagnosis risk for the first medical diagnosis together with the first medical diagnosis on the graphical user interface,
outputting a user query regarding whether an interactive symptom diagnostic needs to be performed for the first medical diagnosis,
based on a determination that an interactive symptom diagnostic does need to be performed for the first medical diagnosis, performing the following further steps:
outputting a symptom user query regarding which of the medical symptoms linked to the first medical diagnosis need to be used for further analysis of the patient data,
applying symptom diagnostic rules for the medical symptoms chosen by the user in the symptom user query to the patient data to define the first diagnosis risk more precisely and to calculate at least one second diagnosis risk for a second medical diagnosis,
outputting the second diagnosis risk together with the second medical diagnosis on the graphical user interface,
wherein every user selection of a further medical symptom is followed by:
freshly applying symptom diagnostic rules for the symptoms chosen by the user in the symptom diagnostic user query to the patient data,
freshly calculating at least one new second diagnosis risk for a new second medical diagnosis being effected dynamically,
updating the output of the freshly calculated new second diagnosis risk together with the new second medical diagnosis on the graphical user interface being effected,
updating the output of the user query regarding which of the medical symptoms linked to the new second medical diagnosis need to be used for further analysis of the patient data being effected;
outputting a user query regarding whether a guideline diagnostic is intended to be performed for the first medical diagnosis,
based on a determination that a guideline diagnostic is intended to be performed, performing the following further steps:
outputting a guideline diagnostic user query regarding which of the medical guideline criteria linked to the previously determined medical diagnosis need to be used for further analysis of the patient data, wherein the previously determined diagnosis is based on the application of the rules or the performance of the symptom diagnostic,
applying the guideline criteria chosen by the user in the guideline diagnostic user query to the patient data in order to define the first diagnosis risk more precisely and in order to calculate at least one third diagnosis risk for a third medical diagnosis,
outputting the third diagnosis risk together with the third medical diagnosis on the graphical user interface.

2. The computer-implemented method as claimed in claim 1, wherein medical diagnoses are output only starting from a predetermined threshold value for the first diagnosis risk and/or in a manner sorted according to the level of the diagnosis risk.

3. The computer-implemented method as claimed in claim 2, wherein the first, second and third diagnosis risks are displayed in the form of a tachograph disk.

4. The computer-implemented method as claimed in claim 3, wherein the diagnosis risk is displayed using color shades on the scale of the tachograph disk.

5. The computer-implemented method as claimed in claim 3, wherein the diagnosis risk is also displayed as a risk probability in the form of a numerical value together with the tachograph disk.

6. The computer-implemented method as claimed in claim 1, wherein, together with the second diagnosis risk, a second operator control element is displayed, wherein the second operator control element is designed for user confirmation, wherein in the event of user confirmation using the second operator control element the second diagnosis risk and the second medical diagnosis are output as a new first diagnosis risk and a new first medical diagnosis on the graphical user interface.

7. The computer-implemented method as claimed in claim 1, wherein the updated output of the freshly calculated new second diagnosis risk is accompanied by fresh updated output of the symptom user query, wherein the updated output of the symptom user query indicates which of the medical symptoms linked to the new second medical diagnosis need to be used for further analysis of the patient data, and wherein medical symptoms previously chosen by the user are retained in the updated output of the symptom user query.

8. The computer-implemented method as claimed in claim 1, wherein every user selection of a further medical symptom is followed by:
freshly applying the guideline criteria chosen by the user in the guideline diagnostic user query to the patient data,
freshly calculating at least one new third diagnosis risk for a new third medical diagnosis being effected dynamically,
updating the output of the freshly calculated new third diagnosis risk together with the new third medical diagnosis on the graphical user interface being effected, and
updating the output of the user query regarding which of the medical guideline criteria linked to the new third medical diagnosis need to be used for further analysis of the patient data being effected.

9. The computer-implemented method as claimed in claim 1, also having the step of conditioning of the patient data, wherein the rules are applied to the patient data only for the conditioned patient data, wherein the data conditioning comprises the filtering of structured data from the patient data.

10. The computer-implemented method as claimed in claim 1, wherein the guideline criteria are applied to define the second diagnosis risk more precisely, said diagnosis risk already having been defined more precisely in the symptom diagnostic.

11. A data processing system having a graphical user interface for medical diagnosis assistance for patient data for a patient, wherein the data processing system is configured to perform steps utilizing a processor, the steps comprising:
- accessing a first database, wherein the first database contains rules, wherein the rules are designed for calculating diagnosis risks for medical diagnoses, wherein the first database also stores the medical diagnoses in combination with medical symptoms,
- applying the rules to the patient data and calculating at least one first diagnosis risk for a first medical diagnosis based on a determination that at least one of the rules can be applied to the patient data,
- outputting the first diagnosis risk for the first medical diagnosis together with the first medical diagnosis on the graphical user interface,
- outputting a user query regarding whether an interactive symptom diagnostic needs to be performed for the first medical diagnosis,
- based on a determination that an interactive symptom diagnostic does need to be performed for the first medical diagnosis, performing the following further steps:
  - outputting a symptom user query regarding which of the medical symptoms linked to the first medical diagnosis need to be used for further analysis of the patient data,
  - applying symptom diagnostic rules for the medical symptoms chosen by the user in the symptom user query to the patient data to define the first diagnosis risk more precisely and to calculate at least one second diagnosis risk for a second medical diagnosis,
  - outputting the second diagnosis risk together with the second medical diagnosis on the graphical user interface,
  - wherein every user selection of a further medical symptom is followed by:
    - freshly applying symptom diagnostic rules for the symptoms chosen by the user in the symptom diagnostic user query to the patient data,
    - freshly calculating at least one new second diagnosis risk for a new second medical diagnosis being effected dynamically,
    - updating the output of the freshly calculated new second diagnosis risk together with the new second medical diagnosis on the graphical user interface being effected,
    - updating the output of the user query regarding which of the medical symptoms linked to the new second medical diagnosis need to be used for further analysis of the patient data being effected;
  - outputting a user query regarding whether a guideline diagnostic is intended to be performed for the first medical diagnosis,
  - based on a determination that a guideline diagnostic is intended to be performed, performing the following further steps:
    - outputting a guideline diagnostic user query regarding which of the medical guideline criteria linked to the previously determined medical diagnosis need to be used for further analysis of the patient data, wherein the previously determined diagnosis is based on the application of the rules or the performance of the symptom diagnostic,
    - applying the guideline criteria chosen by the user in the guideline diagnostic user query to the patient data in order to define the first diagnosis risk more precisely and in order to calculate at least one third diagnosis risk for a third medical diagnosis,
    - outputting the third diagnosis risk together with the third medical diagnosis on the graphical user interface.

12. A non-transitory computer-readable storage medium which stores data which contain instructions for carrying out a computer-aided method for medical diagnosis assistance for patient data by a data processing system, wherein the instructions are executed by a programmed processor, wherein the data processing system has a graphical user interface and performs the following steps:
- accessing a first database, wherein the first database contains rules, wherein the rules are designed for calculating diagnosis risks for medical diagnoses, wherein the first database also stores the medical diagnoses in combination with medical symptoms,
- applying the rules to the patient data and calculating at least one first diagnosis risk for a first medical diagnosis based on a determination that at least one of the rules can be applied to the patient data,
- outputting the first diagnosis risk for the first medical diagnosis together with the first medical diagnosis on the graphical user interface,
- outputting a user query regarding whether an interactive symptom diagnostic needs to be performed for the first medical diagnosis,
- based on a determination that an interactive symptom diagnostic does need to be performed for the first medical diagnosis, performing the following further steps:
  - outputting a symptom user query regarding which of the medical symptoms linked to the first medical diagnosis need to be used for further analysis of the patient data,
  - applying symptom diagnostic rules for the medical symptoms chosen by the user in the symptom user query to the patient data to define the first diagnosis risk more precisely and to calculate at least one second diagnosis risk for a second medical diagnosis,
  - outputting the second diagnosis risk together with the second medical diagnosis on the graphical user interface,
  - wherein every user selection of a further medical symptom is followed by:
    - freshly applying symptom diagnostic rules for the symptoms chosen by the user in the symptom diagnostic user query to the patient data,
    - freshly calculating at least one new second diagnosis risk for a new second medical diagnosis being effected dynamically,
    - updating the output of the freshly calculated new second diagnosis risk together with the new second medical diagnosis on the graphical user interface being effected,
    - updating the output of the user query regarding which of the medical symptoms linked to the new second medical diagnosis need to be used for further analysis of the patient data being effected;

outputting a user query regarding whether a guideline diagnostic is intended to be performed for the first medical diagnosis, based on a determination that a guideline diagnostic is intended to be performed, performing the following further steps:
- outputting a guideline diagnostic user query regarding which of the medical guideline criteria linked to the previously determined medical diagnosis need to be used for further analysis of the patient data, wherein the previously determined diagnosis is based on the application of the rules or the performance of the symptom diagnostic,
- applying the guideline criteria chosen by the user in the guideline diagnostic user query to the patient data in order to define the first diagnosis risk more precisely and in order to calculate at least one third diagnosis risk for a third medical diagnosis,
- outputting the third diagnosis risk together with the third medical diagnosis on the graphical user interface.

* * * * *